US007273963B2

(12) United States Patent
Kneteman et al.

(10) Patent No.: US 7,273,963 B2
(45) Date of Patent: Sep. 25, 2007

(54) MALARIAL ANIMAL MODEL HAVING A CHIMERIC HUMAN LIVER

(75) Inventors: Norman M. Kneteman, Edmonton (CA); John B. Sacci, Jr., Baltimore, MD (US); D. Lorne Tyrrell, Edmonton (CA); John F. Elliott, Edmonton (CA); Abdu F. Azad, Baltimore, MD (US)

(73) Assignees: KMT Hepatech, Inc., Edmonton, Alberta (CA); University of Maryland, Baltimore, Baltimore, MD (US)

( * ) Notice: Subject to any disclaimer, the term of this patent is extended or adjusted under 35 U.S.C. 154(b) by 12 days.

(21) Appl. No.: 11/207,176

(22) Filed: Aug. 17, 2005

(65) Prior Publication Data

US 2006/0156420 A1    Jul. 13, 2006

Related U.S. Application Data

(60) Provisional application No. 60/650,949, filed on Feb. 7, 2005, provisional application No. 60/603,467, filed on Aug. 20, 2004.

(51) Int. Cl.
*G01N 33/00* (2006.01)
*A01K 67/00* (2006.01)
*A01K 67/033* (2006.01)
*A01K 67/027* (2006.01)

(52) U.S. Cl. ............... 800/3; 800/8; 800/9; 800/13; 800/14; 800/18; 800/21

(58) Field of Classification Search ............ None
See application file for complete search history.

(56) References Cited

U.S. PATENT DOCUMENTS

| | | | |
|---|---|---|---|
| 5,652,373 | A | 7/1997 | Reisner |
| 5,698,767 | A | 12/1997 | Wilson et al. |
| 5,709,843 | A | 1/1998 | Reisner |
| 5,804,160 | A | 9/1998 | Reisner |
| 5,849,288 | A | 12/1998 | Reisner |
| 5,849,987 | A | 12/1998 | Reisner |
| 5,858,328 | A | 1/1999 | Reisner |
| 5,866,757 | A | 2/1999 | Reisner |
| 5,980,886 | A | 11/1999 | Kay et al. |
| 5,994,617 | A | 11/1999 | Dick et al. |
| 6,034,297 | A | 3/2000 | Vierling |
| 6,509,514 | B1 | 1/2003 | Kneteman et al. |
| 6,525,242 | B1 | 2/2003 | Wu et al. |
| 2002/0157121 | A1 | 10/2002 | Wu et al. |
| 2003/0115616 | A1 | 6/2003 | Kneteman et al. |
| 2003/0126626 | A1 | 7/2003 | Wu et al. |

FOREIGN PATENT DOCUMENTS

| | | |
|---|---|---|
| EP | 0 438 053 | 7/1991 |
| WO | WO93/07165 | 4/1993 |
| WO | WO94/02601 | 2/1994 |
| WO | WO94/27556 | 12/1994 |
| WO | WO96/18419 | 6/1996 |
| WO | WO98/42824 | 10/1998 |
| WO | WO99/16307 | 4/1999 |
| WO | WO99/46598 | 9/1999 |
| WO | WO 00/17338 | 3/2000 |
| WO | WO 01/32009 A1 | 5/2001 |

OTHER PUBLICATIONS

Morosan et al J Infect Dis., 193(7):996-1004, 2006.*
Wood. Comp. Med. 50(1): 12-15, 2000.*
Sigmund, Arterioscler. Throm. Vasc. Biol.20:1425-1429, 2000.*
Kappel et al. Current Opinion in Biotechnology 3:558-553 1992.*
Sacci et al, *Plasmodium falciparum* infection and exoerythrocytic development in mice with chimeric human livers. Int. J. Parasitol. 36(3):353-360, 2006.*
Badell, et al., "Human malaria in immunocompromised mice: An in vivo model to study defense mechanisms against *Plasmodium falciparum*", J. Exp. Med © The Rockefeller University Press, vol. 192, No. 11, 2002. pp. 1653-1659.
Moore, et al., "Maintenance of the human malarial parasite, *Plasmodium falciparum*, in *scid* mice and transmission of gametocytes to mosquitoes", J. Exp. Med © The Rockefeller University Press, vol. 181, Jun. 1995, pp. 2265-2270.
Moreno, et al., Human malaria in immunocompromised mice: new in vivo model for chemotherapy studies, Antimicrobial agents and chemotherapy, vol. 45, No. 6, Jun. 2001, pp. 1847-1853.
Sacci et al., "Gene expression analysis during liver stage development of *Plasmodium*", International Journal of Parasitology, 32 (2002) 1551-1557.
Sacci et al., "Mouse model for exoerythrocytic stages of *Plasmodium falciparum* malaria parasite", Proc Natl Acad Sci U S A. May 1, 1992;89(9):3701-5.
Tsuji et al., "Establishment of a SCID mouse model having circulating human red blood cells and a possible growth of *Plasmodium falciparum* in the mouse", Vaccine, 1995, vol. 13, No. 15, pp. 1389-1392.
Willimann et al. "In vivo sequestration of *Plasmodium falciparum*-infected human erythrocytes: a severe combined immunodeficiency mouse model for cerebral malaria", J. Exp. Med © The Rockefeller University Press, vol. 182, Sep. 1995, pp. 643-653.
Mercer et al. (2001) "Hepatitis C Virus replication in Mice With Chimeric Human Livers" *Nat. Med.* 7(8): 1-7.
Mullins et al. (1996) "Transgenesis in Non-Murine Species" *J. Clin. Invest. Supp.* 98(11):S37-S40.
Nicolet et al. (1998) "Caractérisation de la Régénération Hépatique Chez la Souris Transgénique Albumine-Urokinase" *Chirurgie* 123(1):47-53.

(Continued)

*Primary Examiner*—Sumesh Kaushal
(74) *Attorney, Agent, or Firm*—Carol L. Francis; Bozicevic, Field & Francis LLP

(57) ABSTRACT

The present invention features a non-human animal model of malaria, e.g., *Plasmodium*, particularly *Plasmodium falciparum*. The model is based on a non-human, immunocompromised transgenic animal having a human-mouse chimeric liver, where the transgene provides for expression of a urokinase-type plasminogen activator in the liver. The invention also features methods for identifying candidate therapeutic agents, e.g., agents having anti-pathogenic activity against malaria.

15 Claims, 11 Drawing Sheets
(9 of 11 Drawing Sheet(s) Filed in Color)

OTHER PUBLICATIONS

Petersen et al. (1998) "Liver Repopulation with Xenogenic Hepatocytes in B and T Cell-deficient Mice Leads to Chronic Hepadnavirus Infection and Clonal Growth of Hepatocellular Carcinoma" *Proc. Nat'l. Acad. Sci. USA* 95:310-315.

Rhim et al. (1994) "Replacement of Diseased Mouse Liver by Hepatic Cell Transplantation" *Science* 263:1149-52.

Rhim et al. (1995) "Complete Reconstitution of Mouse Liver with Xenogeneic Hepatocytes" *Proc. Nat'l. Acad. Sci. USA* 92:4942-4946.

Sandgren et al. (1990) "Complete Hepatic Regeneration After Somatic Deletion of an Albumin-Plasminogen Activator Transgene" *Cell* 66:245-256.

Sarbah et al. (2000) "Hepatitis C: an update on the silent epidemic" *J. Clin. Gastroenterol.* 30(2):125-143.

Sells et al. (1987) "Production of Hepatitis B Virus Particles in Hep G2 Cells Transfected With Cloned Hepatitis B Virus DNA" *Proc. Nat'l. Acad. Sci. USA* 84:1005-1009.

Shapiro, C.N. (1995) "Occupational Risk of Infection with Hepatitis B and Hepatitis C Virus" *Surgical Clinics North Amer.* 75(6):1047-1056.

Toth et al. (1996) "Two Distinct apolipoprotein B alleles in mice generated by a single 'in-out' targeting" *Gene* 178(1):161-168.

Vrancken-Peeters et al. (1997) "Expansion of Donor Hepatocytes After Recombinant Adenovirus-Induced Liver Regeneration in Mice" *Hepatol.* 25(4):884-888.

Wall, R.J. (1996) "Transgenic Livestock: Progress and Prospects for the Future" *Theriogenology* 45:57-68.

Weglarz et al. (2000) "Hepatocyte Transplantation into Diseased Mouse Liver"0 *Am. J. Pathol.* 157(6):1963-1974.

Xie et al. (1998) "Transmission of Hepatitis C Virus Infection to Tree Shrews" *Virology* 244:513-520.

Lieber et al. (1995) "A Modified Urokinase Plasminogen Activator Induces Liver Regeneration Without Bleeding" *Hum. Gene Ther.* 6:1029-1037.

Sureau, C. (1993) "In Vitro Culture Systems for Hepatitis B and Delta Viruses" *Arch. Virol.* 8:3-14.

Pietschmann T, Bartenschlager R. Tissue Culture and Animal Models for Hepatitis C Virus. Clin Liver Dis. Feb. 2003;7(1):23-43.

Bumgardner et al., *Transplantation*, 65(10):53-61 (1998).

Bronowicki et al. (1998) "Hepatitis C Virus Persistence in Human Hematopoietic Cells Injected Into SCID Mice" *Hepatol.* 28:211-218.

Choo et al. (1989) "Isolation of a cDNA clone derived from a blood-borne non-A, non-B viral hepatitis genome" *Science* 244:359-362.

Crabb (2001) "Hard-Won Advances Spark Excitement About Hepatitis C" *Science* 294:506-507.

Cramp et al. (1999) "Hepatitis C virus (HCV) specific immune responses in anti-HCV positive patients without hepatitis C viraemia" *Gut* 44:424-429.

Dandri et al. (2001) "Repopulation of Mouse Liver With Human Hepatocytes and In Vivo Infection With Hepatitis B Virus" *Hepatol.* 33(4) 981-988.

Dhillon et al. (1995) "Pathology of Hepatitis C Virus Infection" *Histopathol.* 26:297-309.

Fausto, N. (2001) "A Mouse Model For Hepatitis C Virus Infection?" *Nat. Med.* 7(8) 890-891.

Fournier et al. (1998) "In Vitro Infection of Adult Normal Human Hepatocytes in Primary Culture by Hepatitis C Virus" *J. Gen. Virol.* 79(Pt 10):2367-2374.

Galun et al. (1995) "Hepatitis C Virus Viremia in SCID® BNX Mouse Chimera" *J. Infect. Dis.* 172:25-30.

Heckel et al. (1990) "Neonatal Bleeding In Transgenic Mice Expressing Urokinase-Type Plasminogen Activator" *Cell* 62:447-456.

Houdebine et al. (1994) "Production of pharmaceutical proteins from transgenic animals" *J. Biotechnol.* 34:269-287.

Houghton, M. (1996) "Hepatitis C Viruses" in: Field's Virology, $3^{rd}$ Edition, Chapter 32, pp. 1035-1036.

Ito et al. (1995) "Cultivation of Hepatitis C Virus In Primary Hepatocyte Culture from Patients with Chronic Hepatitis C Results in Release of High Titre Infectious Virus" *J. Gen Virol.* 77:1043.

Lampertico et al. (1991) "Development and Application of an In Vitro Model for Screening Anti-hepatitis B Virus Therapeutics" *Hepatol.* 13:422-426.

Lerat et al. (1998) "Hepatitis C Virus Transgenic Mice as Model for HCV Associated Liver Disease", *Hepatology* 28(4Pt2):498A.

Lieber et al. (1995) "Adenovirus-mediated Urokinase Gene Transfer Induces Liver Regeneration and Allows for Efficient Retrovirus Transduction of Hepatocytes in vivo" *Proc. Natl. Acad. Sci. Genet.* 92(20):6210-6214.

Liu et al. (1993) "Molecular Cloning and Characterization of cDNA Encoding Mouse Hepatocyte Growth Factor" *Biochim. Biophys. Acta* 1216:299-303.

McBurney et al. (1994) "Murine PGK-1 Promoter Drives Widespread But Not Uniform Expression in Transgenic Mice" *Devel. Dynamics* 200(4): 278-298.

Lieber et al. (1995) "A modified Urokinase Plasminogen Activator Induces Liver Regeneration Without Bleeding" *Hum. Gene Ther.* 6:1029-1037.

Sureau, C. (1993) "In Vitro Culture Systems for Hepatitis B and Delta Viruses" *Arch. Virol.* 8:3-14.

Pietschmann T, Bartenschlager R. Tissue Culture and Animal Models for Hepatitis C Virus. Clin Liver Dis. Feb. 2003;7(1):23-43.

* cited by examiner

A.

B.

C.

MALARIAL ANIMAL MODEL HAVING A CHIMERIC HUMAN LIVER

CROSS-REFERENCE

This application claims the benefit of U.S. Provisional Application No. 60/603,467, filed Aug. 20, 2004, and U.S. Provisional Application No. 60/650,949, filed Feb. 7, 2005, which applications are incorporated herein by reference in their entirety.

GOVERNMENT RIGHTS

This invention was made with partial government support under federal grant no. RO1 AI 47445 awarded by the National Institutes of Health. The United States Government may have certain rights in this invention.

FIELD OF THE INVENTION

The present invention relates generally to animals useful as a model of human malarial infection and of the human malarial life cycle during human disease.

BACKGROUND OF THE INVENTION

Protozoan parasites that belong to the genus *Plasmodium*, are the causative agent for malaria, and are estimated to be responsible for 200-500 million new cases of malaria each year. The parasite has a complex life cycle that involves both extracellular and intracellular forms. Infection is initiated in the host when an anopheline mosquito injects sporozoites during a blood meal feeding. The sporozoites then travel through the vascular system to the liver and invade hepatocytes, thus initiating the exoerythrocytic (EE) stage. Each uninuclear parasite subsequently undergoes division and differentiation to form a mature liver stage schizont with thousand to tens of thousands of uninuclear merozoites. The time for development in the liver stage schizont varies with the species, e.g., 5-7 days for *Plasmodium falciparum*.

At the conclusion of the initial liver stage, thousands of merozoites are released into the bloodstream where they invade erythrocytes. An erythrocytic stage (or "red cell" stage) cycle of 48-72 hr, depending upon the species, then ensues. Some red cell stages will differentiate into male and female gametocytes. Once ingested by a mosquito they can combine and form a zygote, which, upon further development, can produce sporozoites. These sporozoites are later inoculated by the mosquito into another host, thus repeating the cycle.

The sporozoites that are injected by the bite of female *Anopheles* mosquitoes rapidly reach the liver sinusoids. Contrary to earlier assumptions, it is now believed that the numbers of inoculated sporozoites are small, about 10-100 per bite. Whether sporozoites directly penetrate hepatocytes or first travel through endothelial or Kupffer cells lining the sinusoid is still a topic of debate. However, in vitro invasion of hepatic cells suggests that passage through Kupffer cells is not an absolute requirement for EE development. Additionally, evidence from studies done on rats depleted of Kupffer cells has demonstrated that relative to intact animals, Kupffer cell depleted animals had a significant increase in the number of EE stage parasites. This strongly suggests that Kupffer cells are involved in the clearance of sporozoites, not in the facilitation of sporozoite invasion.

Because sporozoites only develop in hepatocytes, it is likely that invasion is mediated by specific interactions between sporozoite proteins and hepatocyte receptors. Sporozoites appear to invade apically by invagination of the hepatocyte cell membrane which forms the parasitophorous vacuole membrane (PVM) surrounding the developing liver stage or exoerythrocytic (EE) parasite. As during merozoite invasion of erythrocytes, material appears to be secreted from sporozoite rhoptries during invasion. Shortly after invading a hepatocyte, the inner membrane and subpellicular microtubules of the thin sporozoite (1.5×10-20 µm) break down, and this area bulges out creating a uninucleated 3-5 µm trophozoite bounded by a plasma membrane situated in a vacuole surrounded by a PVM. The early exoerythrocytic stage parasite develops into a spherical, mature liver stage schizont that occupies most of the volume of the hepatocyte.

During schizogony, parasite antigens are inserted into the PVM which can form deep invaginations into the infected hepatocyte, particularly next to the hepatocyte nucleus. Development of mature EE schizonts containing at least 2,000 uninucleated merozoites takes 42-48 hours for the rodent malarias *P. yoelii* and *P. berghei*. *P. falciparum* liver stage development takes 5-7 days forming up to 30,000 merozoites within a 80-100 µm schizont. During *P. vivax* EE development, some trophozoites do not develop further and may persist as small hypnozoites within hepatocytes for several years. It has been proposed that relapses of *P. vivax* arise from hypnozoites that are triggered to develop by unknown mechanisms. The signals and parasite molecules responsible for the development of a uninucleate sporozoite to a fully mature liver stage schizont and for rupture of this schizont are unknown.

*Plasmodium*-infected hepatocytes have been demonstrated to be an important target of a protective immune response in rodent models of malarial infection. This finding makes the identification and characterization of plasmodial antigens expressed in the infected hepatocyte or exoerythrocytic (EE) stage of the parasite and the immune responses against these antigens crucial for the development of a pre-erythrocytic stage malaria vaccine. A source of EE stage parasites is vital for the selection and characterization of monoclonal antibodies, that identify EE stage antigens, and to characterize the expression of *Plasmodium* genes expressed in infected hepatocytes.

Unfortunately, it is difficult to obtain biological material containing the EE forms of *P. falciparum*. Small quantities of *P. falciparum* EE stage parasites have been produced in primary human hepatocyte cultures and, in a single human hepatoma cell line. The human cell line is difficult to work with and the scarcity of available human liver tissue and low infection rates obtained in the in vitro systems make these approaches less attractive. While mouse forms of malaria exist, *P. falciparum* schizonts develop only in hepatocytes of human, chimpanzee or to a much lower degree in some non-human primates. Chimpanzees have been infected with parasites and liver tissue obtained, by biopsy, for cryosectioning. However, work involving chimpanzees is quite expensive, and does not lend itself to anything more complex than limited tissue harvesting.

There is a need in the field for a reliable small animal model for *P. falciparum* infection. The present invention addresses this need.

SUMMARY OF THE INVENTION

The present invention features a non-human animal model of malaria, e.g., *Plasmodium*, particularly *Plasmodium falciparum*. The model is based on a non-human, immunocompromised transgenic animal having a human-mouse chimeric liver, where the transgene provides for expression of a urokinase-type plasminogen activator in the liver. The invention also features methods for identifying candidate therapeutic agents, e.g., agents having anti-pathogenic activity against *Plasmodium*.

In one aspect the invention provides a non-human animal model of malaria, which can be infected via the normal route of infection, e.g., intravenous delivery. And by natural infectious agent (Malarial sporozoites from Anopheline mosquitoes) as opposed to the use of human RBC's infected with erythrocytic stage falciparum in vitro and then injected into immunodeficient mice to establish infection and maintained by human RBC transfusions.

At least one advantage is that the invention provides an animal model of malaria that can be infected by the normal route of infection, and further provides for the normal development of the parasite in the host.

Another advantage of the invention is that it provides an attractive method for production of a large amount of *P. falciparum* EE stage parasites. The liver tissue can be flash frozen, with some of the tissue cut into thousands of thin sections by cryo-sectioning. Parasite infected cells can be recovered (e.g., by laser capture microdissection) and the RNA isolated for the generation of cDNA. The cDNA can subsequently be used for microarrays or the production of a liver stage cDNA library. Frozen sections can also used to screen monoclonal antibodies or sera generated by the immunization of animals or volunteers with candidate vaccines.

Yet another advantage is that the invention provides a means to recover sufficient liver stage malarial antigen, which can then be used to, for example, develop vaccines targeting the liver stage of infection. The development of a liver stage vaccine can provide a means to prevent the infection ever getting established, since liver stage infection is necessary for maturation of the parasite and occurs before infection of RBC's can occur.

Another advantage of the invention is that it can be used in the study of drugs that target the liver stage parasite.

The invention also provides a model for use in investigation of the process of hepatocyte invasion and methods to prevent this developmental stage.

The invention further provides a model for examining the biology of maturation of the parasite within the hepatocyte and its subsequent process of release, as well as development and screening of therapeutic or prophylactic intervention. Still another advantage of the invention is the parasite can enter the bloodstream after release from the liver, and subsequently invade and infect human red blood cells which have been introduced to the mouse host by transfusion. Thus the model of the present invention also for examination of the process of red cell invasion and the development of gametocytes, and provides the opportunity to screen these as additional targets for therapeutic and preventative intervention. The model of the invention also allows for screening of agents to act as therapeutics that inhibit the red blood cell stage of infection These and other advantages and features of the invention will become apparent to those persons skilled in the art upon reading the details of the animal model and methods of its use as more fully described below.

BRIEF DESCRIPTION OF THE FIGURES

The patent or application file contains at least one drawing executed in color. Copies of this patent or application publication with color drawing(s) will be provided by the U.S. Patent and Trademark Office upon request and payment of necessary fee.

Figure 1:
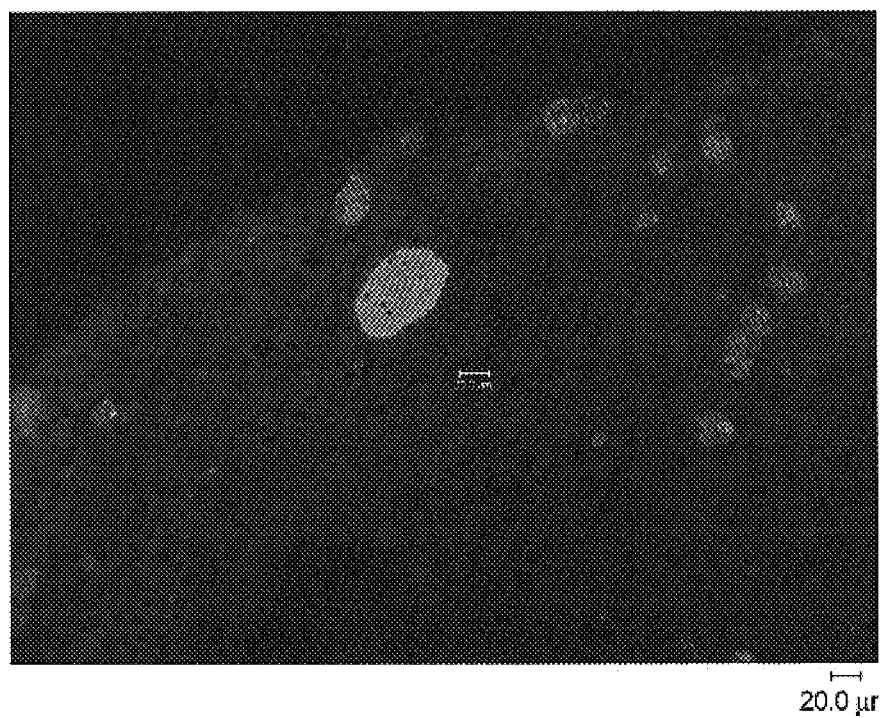
FIGS. 1-2 are photographs of liver tissue of a chimeric mouse of the invention following infection with *P. falciparum* sporozoites. Green staining indicates binding of an antibody that specifically recognizes the heat shock 70 (hsp70) from Plasmodia. The green fluorescence is the specific antibody stain, with the red being an Evan's blue counterstain.

Before the present invention is described, it is to be understood that this invention is not limited to particular methodology, protocols, cell lines, animal species or genera, constructs, and reagents described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a liver cell" includes a plurality of such liver cells and reference to "the non-human animal" includes reference to one or more non-human animals and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Definitions

"Malarial parasite" as used herein, and unless specifically indicated otherwise, and "human malarial parasite" as used herein generally refer to a parasite species of the genus *Plasmodium* which is a causative agent of protozoan disease in humans. There are at least four species of *Plasmodium* which are currently known to cause malaria in humans: *P. falciparum*; *P. vivax*; *P. ovale*; and *P. malariae*. The parasites can be naturally transmitted to the human host by the bite of an infected female mosquito of the genus *Anopheles*. "Human malarial parasite" is not intended to limit the parasites to those immediately recovered for humans; rather it is intended to refer to malarial parasites that can cause human disease. Such human malarial parasites are not normally infectious for non-primate animals.

"Chimeric" as used herein (e.g., "chimeric animal" or "chimeric liver") is meant to describe an organ or animal comprising xenogeneic tissues or cells. Of particular interest is a chimeric animal, wherein the animal is chimeric due to the presence of human hepatocytes engrafted in the animal's liver.

By "immunocompromised" is meant that the animal can not mount a complete or significant immune response against the xenogeneic tissue or cells, e.g., any immune response of the host animal is such that it is ineffective in rejection of the transplanted cells.

The term "transgene" is used herein to describe genetic material which has been or is about to be artificially inserted into the genome of a mammalian, particularly a mammalian cell of a living animal.

By "transgenic animal" is meant a non-human animal, usually a mammal, having a non-endogenous (i.e., heterologous) nucleic acid sequence present as an extrachromosomal element in a portion of its cells or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal according to methods well known in the art. A "transgene" is meant to refer to such heterologous nucleic acid, e.g., heterologous nucleic acid in the form of an expression construct (e.g., for the production of a "knock-in" transgenic animal) or a heterologous nucleic acid that upon insertion within or adjacent a target gene results in a decrease in target gene expression (e.g., for production of a "knock-out" transgenic animal).

A "knock-out" of a gene means an alteration in the sequence of the gene that results in a decrease of function of the target gene, preferably such that target gene expression is undetectable or insignificant. Transgenic knock-out animals can be comprise a heterozygous knock-out of a target gene, or a homozygous knock-out of a target gene. "Knock-outs" as used herein also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

A "knock-in" of a target gene means an alteration in a host cell genome that results in altered expression (e.g., increased (including ectopic) or decreased expression) of a target gene, e.g., by introduction of an additional copy of the target gene, or by operatively inserting a regulatory sequence that provides for enhanced expression of an endogenous copy of the target gene. "Knock-in" transgenics can comprise a heterozygous knock-in of the target gene or a homozygous knock-in of a target gene. "Knock-ins" also encompass conditional knock-ins.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest.

The term "therapeutic agent" as used herein refers to any molecule, e.g., protein or small molecule, pharmaceutical compound, antibody, antisense molecule, ribozyme, and the like, useful in the treatment of a disease or condition, e.g., a liver condition such as that associated with infection by *Plasmodium*. For example, therapeutic agents of the invention include molecules that inhibit, ameliorate, or relieve symptoms (e.g., symptoms that can be observed in tissue, e.g., by histology or molecular analysis) associated with plasmodial infection, and in particular by infection with *P. falciparum*.

The term "infection" as used in the context of an animal model described herein infected with a malarial parasite, is meant to refer to the state of an animal from which malarial parasites can be recovered, where the animal may or may not exhibit any or all clinical symptoms associated with malarial infection.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease.

The term "unit dosage form" as used herein refers to physically discrete units suitable as unitary dosages for subjects (e.g., animals, usually humans), each unit containing a predetermined quantity of agent(s) in an amount sufficient to produce the desired effect in association with a pharmaceutically acceptable diluent, carrier or vehicle. The specifications for the novel unit dosage forms of the present invention will depend on a variety of factors including, but not necessarily limited to, the particular agent employed and the effect to be achieved, and the pharmacodynamics associated with each compound in the host.

OVERVIEW

The present invention is based on the development of a murine animal model having a chimeric liver with human hepatocytes, and which supports infection by a human malarial parasite, e.g., a species of *Plasmoidum* which is a causative agent of malaria in humans.

The murine animal model generally involves transplantation of human hepatocytes into the liver of a transgenic mouse host at an appropriate stage of the host's development, preferably shortly after birth of the host.

To the best of the inventors' knowledge, the present invention for the first time provides a non-primate host, with reliably achieved and stable human hepatocyte engraftment, for use as a model of malaria infection in humans, where the animal model can be infected through the normal route of infection (e.g., by intravenous inoculation, and which can support infection of the liver and development of parasites through all stages of the malarial life cycle. This aspect of the invention is particularly important for use in the development of anti-malarial agents, since the animal model provides the ability to screen for agents that inhibit malaria at any of various stages of its life cycle, including the pre-erythrocytic stage, liver stage of infection, and erythrocytic, as well as during the processes involved in development and transmission of one life stage to the next.

Accordingly the invention features a chimeric animal as described above, which is infected with one or more stages of a human malarial parasite. In addition the invention features methods of using the malarial-infected chimeric animal model described herein, including methods of identifying agents for treatment or prevention of infections by a human malarial parasite.

The invention will now be described in more detail.

Host Animals

The host animal is generally a non-human, immunocompromised mammal having an increased production in the liver of urokinase-type plasminogen activator (uPA) and in which human hepatocytes can be engrafted and maintained. Exemplary non-human animals upon which the animal model of the invention can be based include, but are not necessarily limited to, mice, rats, guinea pigs, hamsters, sheep, pigs, primates, and the like. In one embodiment, the host animal is of the genus *Rodentia*, preferably a mouse. In a preferred embodiment, the host animal is an immunocompromised mouse, preferably an immunocompromised mouse transgenic for urokinase-type plasminogen activator (uPA), more preferably an immunocompromised mouse comprising a transgene that provides for liver-specific production of uPA (e.g., an Alb-uPA transgene, see, e.g., Heckel et al *Cell* 62:447 (1990)). Mice suitable for use in the present invention can be produced from any of a variety of background strains including, but not necessarily limited to, the strains C.B-17, C3H, BALB/c, C57131/6, AKR, BA, B10, 129, etc. The host animal may be either male or female.

Immunocompromised Background

As noted above, the host animal is preferably immunocompromised. Immunocompromised mammalian hosts suitable for implantation and having the desired immune incapacity are available. Alternatively, though less preferred, immunocompromised animals can be generated from immunocompetent animals by, for example, administration of one or more compounds (e.g., cyclosporin) and other methods well known in the art. In general, the immunocompromised host can not mount a complete immune response against the xenogeneic tissue or cells.

Of particular interest are animals that are immunocompromised due to a genetic defect that results in an inability to undergo germline DNA rearrangement at the loci encoding immunoglobulins and T-cell antigen receptors. Also of interest are immunocompromised animals that have one or more genetic defects that leads to significantly decreased numbers of or no detectable functional T cells or B cells.

In one embodiment, the innate immune system of the animal is at least partially intact, such that the animal has at least detectable up to native natural killer cell and/or macrophage activity relative to a normal animal (e.g., relative to a normal mouse, particularly of the same genotype). Of particular interest is a mouse having both a scid mutation and an innate immune system that is at least partially intact (e.g., has at least detectable up to native natural killer cell and/or macrophage activity).

In another embodiment, the animals have the beige mutation (bg), which is associated with a natural killer (NK) cell deficiency. In one embodiment, mice are produced having both the scid mutation and the bg beige mutation, resulting in an animal that does not mount an effective immune response to allogeneic or xenogeneic cells or tissues introduced to the organisms Of particular interest are mice that have a homozygous mutation at the scid locus (scid/scid). The scid mutation is associated with a deficiency in DNA-dependent protein kinase catalytic subunit and prevents VDJ recombination in immunoglobulin and T-cell receptor genes. Animals homozygous for the scid mutation lack functionally recombined immunoglobulin and T-cell receptor genes and thus are deficient in both T and B cell lineages. The scid/scid mutation is available or may be bred into a number of different genetic backgrounds, e.g., CB.17, ICR (outbred), C3H, BALB/c, C57B1/6, AKR, BA, B10, 129, etc.

Other exemplary immunocompromised host that are presently available include transgenic mice genetically engineered to lack the recombinase function associated with RAG-1 and/or RAG-2 (e.g., commercially available TIM™ RAG-2 transgenic), to lack Class I and/or Class II MHC antigens (e.g., the commercially available C1D and C2D transgenic strains), or to lack expression of the Bcl-2 proto-oncogene. Other mice that may be useful as recipients are NOD scid/scid; SGB scid/scid, bh/bh; CB.17 scid/hr; NIH-3 bg/nu/xid and META nu/nu. Transgenic mice, rats and pigs are available which lack functional B cells and T cells due to a homozygous disruption in the CD3F-gene. Immunocompromised rats include HsdHan:RNU-rnu; HsdHan:RNU-rnu/+; HsdHan:NZNU-rnu; HsdHan:NZNU-rnu/+; LEW/HanHsd-rnu; LEW/HanHsd-rnu/+; WAG/HanHsd-rnu and WAG/HanHsd-rnu/+. In one embodiment of interest, the animal is an immunodeficient mice having both a Rag and a common gamma chain knockout (and thus, substantially no T, B or NK cells).

Transgenic Expression of Urokinase

As discussed above, the chimeric animal of the invention is also a "knock-in" transgenic for expression of urokinase-type plasminogen activator (uPA). In one embodiment, the transgene is the Alb-uPA transgene, which comprises a murine albumin enhancer/promoter, the murine uPA gene coding region, and the 3' untranslated and flanking sequences of the growth hormone gene (Heckel et al. *Cell* 62:447-56 (1990); Sandgren et al. *Cell* 66:245-56 (1991)). Preferably the animal is homozygous, rather than heterozygous, for the urokinase-type plasminogen activator transgene. The Alb-uPA transgene results in a lethal insult to hepatocytes that carry it, and also results in a high local (intrahepatic) concentration of urokinase, which in turn processes hepatocyte growth factor to its active form within the liver. Without being held to theory, viable allogeneic or xenogeneic cells introduced at an appropriate time in the development of an Alb-uPA transgenic animal are stimulated to replicate in this environment. The donor cells thus grow to "replace" the endogenous hepatocytes that die as a result of the lethal insult of the transgene.

Isolation of Human Hepatocytes and Other Cells Suitable for Transplantation

Human hepatocytes for transplantation into the host animals are isolated from human liver tissue by any convenient method known in the art. In general, the human hepatocytes may be fresh tissue (e.g., obtained within hours of death), or freshly frozen tissue (e.g., fresh tissue frozen and maintained at or below about 0° C.). Ideally, the cells used are recently isolated (i.e., within 2 to 4 hours) from freshly obtained human liver tissue. Human hepatocytes that are placed in a defined cryopreservation media may be stored for long periods of time (e.g., in liquid nitrogen) and thawed as required, thus permitting the development of banks of stored hepatocytes. In general, it is usually important that the isolation procedure and handling and storage protocol serve to minimize warm ischemia following cessation of blood flow to the liver (e.g., generally less than about 30 min to 60 min, preferably less than about 20 min to about 40 min) and to minimize cold ischemia that may result from storage (e.g., generally less than about 12 hr, usually less than about 1 hr to 2 hrs). In one embodiment, the human tissue is normal, e.g., having no detectable pathogens, normal in morphology and histology, and essentially disease-free). Usually the period of warm ischemia exposure is not more than about 20-50 minutes.

The liver tissue can be dissociated mechanically or enzymatically to provide a suspension of single cells, or fragments of intact human hepatic tissue may be used. In a preferred embodiment, the hepatocytes are isolated from donor tissue by routine collagenase perfusion (Ryan et al. *Meth. Cell Biol.* 13:29 (1976)) followed by low-speed centrifugation. Hepatocytes can then be purified by filtering through a stainless steel mesh (e.g., 100 μm), followed by density-gradient centrifugation. Alternatively, other methods for enriching for hepatocytes can be used, e.g., fluorescence activated cell sorting, panning, magnetic bead separation, elutriation within a centrifugal field, etc. The final suspension used for implantation generally comprises at least about 50-75% hepatocytes, usually at least about 80-99% hepatocytes, generally with viability by trypan blue exclusion of 80-99%, In another embodiment, the cells to be transplanted are human stem cells or hepatocyte precursor cells which, following transplantation into the host animal's liver, develop or differentiate into human hepatocytes susceptible to malarial infection. In one specific embodiment, the human stem cells are obtained from human umbilical cord blood cells. Human umbilical cord blood cells are not only a source for stem cell reconstitution of hepatocytes, but also for reconstitution of the immune system (see, e.g., Verstegen et al. Blood. 91(6):1966-76 (1998)).

Transplantation of Human Hepatocytes or Other Suitable Cells into Hosts

The timing of the introduction of the donor hepatocytes into the transgenic, immunocompromised host may be important to the production of a chimeric liver populated with a number of human hepatocytes sufficient to render the chimeric liver susceptible to infection by a malarial parasite and to support its replication and development. This may be particularly true where the parasite is expected to exhibit low infectivity and/or low replication rates.

Where the animal is murine (e.g., a mouse), the host is ideally less than 10 days to 2 weeks in age, and optimally about 7 to 10 days old, or less than or about one week (i.e., less than or about 5 to 7 days old or younger), at the time of transplantation. In general, the transplantation is preferably carried out between about 8-10 days and 15 days of age. The window for transplant can be widened to about 7-18 days of age to gain flexibility while maintaining good results. In general, hepatocyte transplantation at 5-12 days of age is of most interest, with hepatocyte transplantation at 4 days of age requiring p technically gifted staff, with hepatocyte transplantation beyond 12 days of age being associated with a decline in overall transplantation success rate. Without being held to theory, the timing of transplantation indicated herein is a compromise between excess technical mortality associated with very early transplantation (i.e., due to the small size of the animals) and the time for maximal replicative stimulus (e.g., the number of cell divisions in the recipient liver that occur before transplant may influence the success and extent of engraftment of the donor human cells). Furthermore, timing of transplantation is also important since the stimulus for liver cell repopulation provided by the transgene diminishes with time, and is generally depleted after the recipient is more than about 6 weeks old (Rhim et al. (1994) Science 263:1149-52; about 10-12 weeks for homozygotes).

The human hepatocytes (or other suitable cell, e.g., hepatocyte precursor or stem cell) can be transplanted using any suitable method known in the art. Preferably, the human hepatocytes are injected intrasplenically, e.g., into the inferior splenic pole.

Successful engraftment can be monitored by conventional methods, e.g., by examining the levels of human liver-specific proteins in the host serum, e.g., human serum albumin (HA), or human alpha-1 antitrypsin. The chimeric host can be used for experimentation (e.g., for infection with a malarial parasite, to screen candidate agents, etc.) when suitable. Where the animal is to be infected with a parasite of relatively low infectivity and/or low replicative capacity, the chimeric animal can be inoculated within about four to six weeks post-transplant, generally at about six weeks post-transplant, and may be as early as three weeks post-transplant.

In general, the animal host develops human chimerism within its liver such that the percentage by volume of liver cells that are human liver cells are from at least about 20% to 50%, generally about 40% to 60% or more, and may be optimized to 90% or more. The chimeric animal can be maintained with functional transplanted hepatocytes for at least several weeks, generally at least about 5 weeks, more usually at least about 12 weeks to 24 weeks, up to 8 months or more, and may be up to the lifespan of the host.

Production of Chimeric Animals having Human Red Blood Cells

In one embodiment of interest, the chimeric animals of the invention are provided with human red blood cells (RBCs), so as to facilitate or support the erythrocytic stage of the human malarial life cycle.

For example, a chimeric animal of the invention can be infected with P. falciparum sporozoites, then transfused intraperitoneally with 1.0 ml of washed human red blood cells (RBCs) on 2 consecutive days. This will render the animals circulating red blood cell population 75-95% human. Alternatively, human erythroid cell production in the chimeric mouse model can be established by transfer of human stem cells of origin from human umbilical cord blood, or human fetal liver cell preparations.

Regardless of the method in which it is accomplished, the chimeric animal can be produced having from, for example, at least about 40% up to about 95% or more human RBCs, at least about 50% to about 90% human RBCs, at least about 60% to about 85% human RBCs, at least about 70% to about 85% human RBCs, or at least 45% to about 60% human RBCs. For example, intraperitoneal transfusion of 1 ml washed human RBC's for 2 consecutive days can result in mice with 80-95% human circulating RBC's and that this is maintained for at least 3 days.

Regardless of the method use, providing human red blood cells in the animal allows the malarial merozoites to leave the hepatocytes and enter the human red blood cells. Given that the peripheral red blood cells will contain a substantial proportion of human red blood cells, peripheral smear examination or PCR for malarial parasites can be used to establish the redevelopment of the erythrocytic stage of the malarial life cycle. In addition, such infected chimeric animals can facilitate transfer of malarial parasites by mosquito to a second host chimeric animal, thus providing the entire malarial life cycle in the model.

The inventors have shown that homogenates of mouse liver harvested 7 days after infection with P. falciparum can successful infect human RBC's in vitro for 24, 48, and 72 hours as confirmed by microscopic examination of Giemsa stained slides of RBC preps after in vitro introduction of parasites to RBC cultures.

Malarial Parasites and Infection

Methods for obtaining malarial parasites and administration to a mammal are well known in the art. For example, infected Anopheline mosquitoes are obtained from the Malaria Program at the Naval Medical Research Center, Silver Spring, Md. The mosquitoes are microdissected and the salivary glands, containing the sporozoites are triturated in a ground-glass homgenizer, counted and injected intravenously ($0.1-3\times10^6$ parasites/mouse)into the mice. The number of parasites that are injected depends upon the specific study as well as the recovery of sporozoites from the mosquitoes. The specific procedures for the recovery of P. falciparum sporozoites are well known in the art and are common practice for investigators in the field of Plasmodium.

The P. falciparum parasite takes approximately 7-9 days to mature in the hepatocyte and will subsequently be released from the hepatocyte to infect erythrocytes. Thus, there is no chronic state of infection with P. falciparum. However P. vivax can form hypnozoites that remain in the liver in a developmentally arrested state for an extended period of time (months to years). For reasons that are not understood, P. vivax hypnozoites will re-initiate development and mature in the hepatocyte. The ability to study this phenomenon is yet another advantage and feature of the invention, as such can not be studied in an in vitro system but can be assessed in the chimeric animal model of the invention.

The parasitic load of the infected host can be determined. The parasitic load can be determined either qualitatively or quantitatively by, for example, examination of tissue (e.g., liver cells, blood smears), PCR (e.g., real-time PCR assays), and the like. For example, real-time quantitative PCR (RTQ-PCR) can be utilized to determine the parasite burden in the livers and blood of P. falciparum infected chimeric animals. The small subunit (18S) ribosomal RNA gene of Plasmodium is a well conserved gene that can be used as a target for RTQ-PCR. For quantitative analysis, a standard curve can be constructed using DNA that is extracted from known concentrations of blood stage parasites. DNA from liver stage samples is extracted and used in a RTQ-PCR assay with DNA from known concentrations of parasites. A cycle threshold (Ct) versus parasite number is produced for the standard and the number of parasites in the liver calculated by plotting the CT of the liver stage samples.

The parasitic load of the infected host over time can mimic that observed in human infection, which correlates with the development of the parasite during is natural life cycle. Thus the invention encompasses chimeric hosts having EE stage parasites (liver stage parasites, including developing intrahepatic merozoites) as well as erythrocytic stage (or "red cell" stage) parasites (including trophozoites). In general, the chimeric animal can be provided so as to support all or part (e.g., pre-erythrocytic) of the malarial life cycle. That is, the animal model of the invention can support the entire life cycle of the malarial parasite (e.g., *P. falciparum*) through all stages, which can include transfer of blood-borne parasites from one infected chimeric animal to another (e.g., by artificial transfer for by mosquito).

In general, in *P. falciparum* the liver stage generally occurs only within about the first 2 weeks (e.g., 10 days or less) of infection. Subsequently, the malarial parasites are only in the blood stage where they infect red blood cells, develop, and then are released and infect RBCs again to increase the numbers of parasites. Use of the animal model of the invention to identify agents that can inhibit any of these stages of malarial parasite development is contemplated by the present invention, with agents that are suitable for treatment of the most malaria patients are those that can affect the red blood cell stage parasite being of particular interest.

Infection of the chimeric animals of the invention can be established with introduction into the animal (e.g., into the animal's bloodstream) of about 10, 100, $5 \times 10^2$, $10^3$, $5 \times 10^3$, $10^4$, $5 \times 10^4$, $10^5$, $5 \times 10^5$, $10^6$, $5 \times 10^6$, or $10^7$, usually of about 10, 100, $5 \times 10^2$, $10^3$, $5 \times 10^3$, $10^4$, $5 \times 10^4$, $10^5$, $5 \times 10^5$, $10^6$ or fewer parasites. The parasitic load of the infected chimeric animals of the invention at the liver stage (e.g., 5-7 days after infection) can be about $10^4$, $5 \times 10^4$, $10^5$, $5 \times 10^5$, $10^6$, $5 \times 10^6$, $10^7$, $5 \times 10^7$, or $10^8$ or more. The parasitic load of the infected chimeric animals of the invention at the red cell stage can be about $10^4$, $5 \times 10^4$, $10^5$, $5 \times 10^5$, $10^6$, $5 \times 10^6$, $10^7$, $5 \times 10^7$, or $10^8$ or more.

In some embodiments, malarial infection of a chimeric animal of the invention is maintained for at least 3 days, 5 days, 6 days, 7 days, 8 days or more, where longer periods of infection which involve the erythrocytic stage of the parasite are maintained in chimeric animals having human RBCs, e.g., as described above.

Screening Assays

The chimeric animal of the invention can be used in a variety of screening assays suitable for identification of agents that inhibit malarial infection, development, replication, and the like. To this end, the animal model of the invention is used to screen candidate agents for such effects.

The screening assays described herein can be used with chimeric animals having a malarial infection at any stage of the malarial life cycle, including the EE stage of infection (which includes the liver stage) and the erthrocytic stage of infection. Thus the invention encompasses screening for agents that affect a malarial parasite at any stage, including to inhibit infection of hepatocytes by sporozoites, inhibit development within hepatocytes, inhibit release of merozoites from hepatocytes, inhibit infection of red blood cells by merozoites, inhibit development within red blood cells, inhibit release of merozoites, and the like.

"Candidate agents" is meant to include synthetic, naturally occurring, or recombinantly produced molecules (e.g., small molecule; drugs; peptides; antibodies (including antigen-binding antibody fragments, e.g., to provide for passive immunity) or other immunotherapeutic agents; endogenous factors present in eukaryotic or prokaryotic cells (e.g., polypeptides, plant extracts, and the like)); etc.). Of particular interest are screening assays for agents that have a low toxicity for human cells.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In one embodiment, the animal model of the invention is used to identify agents that ameliorate symptoms caused by malarial infection (where symptoms include tissue pathology) and/or to more directly affect a pathogenic mechanism of the infecting parasite, e.g., inhibit parasite infection, decrease parasitic replication at one or more stages of the life cycle, or otherwise disrupt the malarial life cycle. In general, the candidate agent is administered to the animal model of the invention, and the effects of the candidate agent assessed relative to a control (e.g., relative to an uninfected animal, relative to a *malaria*-infected animal treated with an agent having a known anti-malarial effect (e.g., chloroquine; malarone; artemisinin compounds, especially artesunate, artemether and dihydroartemisinin, and the like). For example, the candidate agent can be administered to a malaria-infected animal of the invention, and the parasitic titer of the treated animal (e.g., as measured by RT-PCR of blood or liver samples) compared to the parasitic titer of the animal prior to treatment and/or to a control, untreated malaria-infected animal. In general, a detectable and significant decrease in parasite titer of an infected animal following treatment with a candidate agent is indicative of anti-malarial activity of the agent.

The candidate agent can be administered in any manner desired and/or appropriate for delivery of the agent in order to effect a desired result. For example, the candidate agent can be administered by injection (e.g., by injection intravenously, intramuscularly, subcutaneously, or directly into the tissue in which the desired affect is to be achieved), orally, or by any other desirable means. Normally, the in vivo screen will involve a number of animals receiving varying amounts and concentrations of the candidate agent (from no agent to an amount of agent that approaches an upper limit of the amount that can be delivered successfully to the animal), and may include delivery of the agent in different formulations and routes. Moreover, the agents may be administered to the animals at various stages of the parasite's life cycle, as described above, with administration when the host contains liver stage parasites being of particular interest. The agents can be administered singly or can be combined in combinations of two or more, especially where administration of a combination of agents may result in a synergistic effect.

The activity of the candidate agent can be assessed in a variety of ways. For example, the effect of the agent can be assessed by examining blood samples for the presence of the parasite (e.g., titer) or markers associated with the presence of the pathogen (e.g., a pathogen-specific protein (*P. falciparum* histidine-rich protein II) or encoding nucleic acid, etc.)

Qualitative and quantitative methods for detecting and assessing the presence and severity of malarial infection are well known in the art.

The best known technology for the rapid determination of plasmodial infection is the immunochromatographic strip. In this format a monoclonal antibody that is specific for a *P. falciparum* protein is immobilized onto a nitrocellulose strip and is used to capture an antigen that is found in the blood of an infected individual. The prevailing test uses capture of Pf histidine-rich protein. In field studies, the test strips have been shown to be capable of detecting <500 parasites/µl. This is an exemplary technology that can be utilized to assess parasite levels in the blood of infected chimeric animals of the invention.

In one embodiment, the activity of an agent against malarial infection can be assessed by examining blood samples and/or tissue sections for the presence of a malarial parasite (e.g., by RT-PCR, antibody binding using anti-malarial antigen antibodies, etc.). In another embodiment, the activity of an agent against malarial infection can be assessed by examining serum samples for the presence of malarial nucleic acid or antigens. Alternatively or in addition, the host liver may be biopsied and in situ, and malarial nucleic acid or malarial antigens detected to demonstrate directly any qualitative or quantitative alterations in the level of parasites within tissue sections. Alternatively or in addition, the host can be euthanized and the liver examined histologically for signs of infection.

Identified Agents

The compounds having the desired pharmacological activity may be administered in a physiologically acceptable carrier to a host for treatment. The therapeutic agents may be administered in a variety of ways, orally, topically, parenterally e.g. subcutaneously, intraperitoneally, intravascularly, by inhalation, etc. Depending upon the manner of introduction, the compounds may be formulated in a variety of ways. The concentration of therapeutically active compound in the formulation may vary from about 0.1-100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying Agents, salts for varying the osmotic pressure or buffers for securing an adequate pH value, and skin penetration enhancers can be used as auxiliary agents.

Vaccine Development

With some modifications, the animal model of the invention can also be used to screen candidate vaccines for their ability to prevent or ameliorate infection by a malarial parasite. In general, a "vaccine" is an agent that, following administration, facilitates the host in mounting an immune response against a target pathogen. The humoral, cellular, or humoral/cellular immune response elicited can facilitate inhibition of infection by the pathogen against which the vaccine is developed. Of particular interest in the present invention are prophylactic vaccines that elicit a protective immune response that inhibits infection by and/or intrahepatic replication of a malarial parasite. Also of interest are therapeutic vaccines which provide protection through provision of passive immunity or rapidly upregulated specific active immunity (e.g., anti-malarial immunoglobulin, and the like).

In this embodiment of the invention, the immune system of the immunocompromised chimeric animal is reconstituted using, for example, stem cells, peripheral blood mononuclear cells (PBMCs), blood cord cells, hematopoietc cells, or other suitable cells of human origin to provide for a human immune system in the animal. Methods for isolating human immune cells and reconstitution of the immune system of an immunocompromised animal, e.g., a mouse with an human immune system are well known in the art (see, e.g., *Nature* 335:256-59; *Proc. Natl. Acad. Sci.* USA 93(25):14720-25). In one embodiment, the human immune cells are obtained from the same donor as the human hepatocytes used in the production of the chimeric liver. In one embodiment, the human immune cells are introduced into the host according to methods well known in the art, e.g., by intraperitoneal injection.

An alternate approach involves transplantation of the chimeric mouse with human fetal liver cells which may effect repopulation with both human hepatocytes and immune cells and/or erythrocyte lineage cells. This provides reconstitution of the animal with a human immune system and/or a human red blood cell lineage.

The invention also contemplates use of the chimeric animals with liver stage infection as a source for antigens from the liver stage infection as putative targets for vaccine development. In another embodiment, the chimeric mouse can be developed having a background of, for example, a Rag 2/common gamma chain knockout to facilitate reconstitution with human immune system.

Screening for an effective vaccine is similar to screening methods described above. In short, the candidate vaccine is administered to the chimeric animal prior to inoculation with the malarial parasite. The candidate vaccine is generally administered by providing a single bolus (e.g., intraperitoneal or intramuscular injection, topical administration, or oral administration), followed by one or more booster immunizations. The induction of an immune response can be assessed by examining B and T cell responses that are specific for parasite antigens according to methods well known in the art. The immunized animal is then challenged with the parasite; normally several immunized animals are challenged with increasing numbers of the parasite. The immunized animals and non-immunized control animals are then observed for development of infection, and the severity of infection assessed (e.g., by assessing the level of parasite present, examining human hepatocyte function parameters, etc.). Vaccine candidates that provide for a significant decrease in infection by the malarial parasite and/or a significant decrease in the severity of disease that results post-challenge are identified as viable vaccines.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials were used in the examples below.

Parasites

All experiments utilized sporozoites or blood stage parasites of the NF54 strain of *Plasmodium falciparum*. Sporozoites were reared in *Anopheles stephensi* mosquitoes. Sporozoites were isolated by hand dissection or by a discontinuous gradient$_{18}$ in Medium 199 (Gibco, Grand Island, N.Y.) with 5% fetal calf serum.

Mice

Five to fourteen day old SCID mice homozygous for the urokinase type plasminogen activator transgene received inoculation by intrasplenic injection with $10^6$ human hepatocytes that had been isolated (with informed consent) from surgically resected liver specimens by collagenase digestion and Percoll gradient centrifugation (Ryan et al., Surgery 113:48-54 (1993); Seglen Methods Cell Biol., 13:29-83 (1976)). Mice were screened 6 weeks post transplant for successful engraftment by serum analysis for human alpha one antitrypsin by ELISA (Seglen (1976)). Mice were cared for by the University of Alberta Health Sciences Laboratory Animal Services according to the guidelines of the Canadian Council on Animal Care and under protocols approved by the University of Alberta Faculty of Medicine and Dentistry Health Sciences Laboratory Animal Ethics Committee.

Infection with Sporozoites and Tissue Collection

The mice first received an intravenous tail vein injection of $1-1.5\times10^6$ *P. falciparum* sporozoites. The mice were then euthanized by CO2 overdose between 3 and 8 days post-infection and their livers removed for cryosectioning or RNA extraction. Livers were rinsed in PBS and the lobes cut into separate pieces. Selected lobes were embedded in Tissue-Tek O.C.T. compound (Miles Scientific, Naperville, Ill.) and frozen in an isopentane/liquid $N_2$ bath, while other fragments were flash frozen in liquid $N_2$ for RNA extraction. Tissue sections (7 μm) were cut on a Leica CM1900 (Leica Microsystems, Deerfield, Ill.), fixed in absolute methanol, and stored at $-80°$ C. until used.

Human α1-Antitrypsin ELISA Assay

IMMULON™-2 96 well plates (Coming, Inc.) were coated overnight at 4° C. with 50 μl of primary antibody (Goat-anti-human □-1-antitrypsin, Oxoid Inc., Nepean, Ont., Canada) diluted 1:1000 with coating buffer (0.1M NaHCO$_3$, pH 9.5) to each well. Wells were then washed once with Tris-buffered saline (50 mM Tris, 100 mM NaCl) containing 0.025% (v/v) Tween 20 (TBS-T) prior to a second incubation overnight at 4° C. with blocking buffer (TBS-T containing 5% skim milk powder). Wells were washed twice with TBS-T prior to addition of serum samples that had been diluted in blocking buffer. Sera from non-transplanted Alb/uPA mice and from humans were used as negative and positive controls, respectively. Serial dilutions of the human reference serum, Calibrator 4 (Oxoid Inc., Nepean, Ont., Canada) were used for constructing a standard curve. After 2 hours at room temperature, the wells were washed three times with TBS-T prior to incubation for 2 hours at room temperature with the primary antibody linked to horseradish peroxidase (HRP). Conjugation of the primary antibody with HRP was done using the EZ-Link Plus Activated Peroxidase Kit (Pierce, Rockford, Ill.) according to the manufacturer's instructions. Wells were washed 3 times with TBS-T and 50 μl of a HRP substrate solution (1 mg of 3,3',5,5'-tetramethyl benzidine dihydrochloride (Sigma, Oakville, Ont., Canada) in 0.05M phosphatecitrate buffer, pH 5 with freshly added $H_2O_2$ (0.02% v/v) was added for exactly 5 min. Reactions were terminated by the addition of 50 μl 2N $H_2SO_4$ to each well and HRP activity determined by spectrophotometry at an absorbance of 450 nm. Serum levels of hAAT were calculated from the standard curve that was generated by the human reference standard.

Antibodies

Several different monoclonal antibodies and polyclonal antisera were used for the immunofluorescent assays (IFA). The anti-CS monoclonal antibody (mAb), 2A10, bound to the repeat region of the CS protein and was specific for *P. falciparum* (Nardin et al., J. Exp. Med. 156:20-30 (1982)). The anti-SSP2 mAb (PfSSP2.1), produced by immunization of mice with a PfSSP2 recombinant protein (Charoenvit et al., Infect. Immun. 65:3430-3437 (1997)) was also specific for *P. falciparum*. The HSP70 mAb (Tsuji et al., Parasitol. Res. 80:16 (1994)) was generated against *P. berghei* parasites, but cross-reacts with *P. falciparum*. EXP- 1 anti-sera was raised by immunization of rabbits with a DNA vaccine construct containing the full-length gene. LSA-1 anti-serum was raised, in rabbits, by immunization with a multiple antigenic peptide (MAP) (Tam et al., J. Immunol. Methods 124:53-61 (1989)) that contained 8 copies of a 15-mer LSA-1 repeat (LEQERLAKEKLQEQQ (SEQ ID NO:01)) (Zhu et al., Mol. Biochem. Parasitol. 48:223-226 (1991)). EBA-175 anti-serum was produced by immunization of mice with peptide sequences from region VI of the PfEBA-175 molecule. The mAb against MSP-1 was produced by immunization of mice with *P. falciparum* merozoites and subsequent fusion of immune spleen cells with a myeloma cell line (Lyon et al., J. Immunol. 138:895-901 (1987)).

Immunofluorescence Assay

Slides with tissue sections were stored at $-70°$ C. wrapped in foil and a plastic bag. Tissue section slides are removed from the freezer, placed in a dessicator and allowed to equilibrate to room temperature. One hundred microliters of the diluted antisera was then applied to the tissue section (this is a volume sufficient to cover the tissue). Slides were then incubated for 30 minutes at 37° C. in a humidity chamber. Liver section slides were removed from the humidity chamber, placed in a staining dish and washed 3 times for 5 minutes with PBS. A fluorescein conjugated IgG (Kirkegaard and Perry, Gaithersburg, Md.) was used as the secondary antibody. The specificity of the secondary antibody varied depending upon the species of the primary antibody used to stain the sections. The secondary antibody was diluted 1:40 into PBS containing 0.02% Evans blue. The Evans blue was added to act as a counterstain to suppress any autofluorescence in the tissue. The diluted secondary antibody was added and the slides placed in a humidity chamber, in the dark, and incubated at 37° C. for 30 minutes. Tissue sections were then washed as above and the slides mounted, using VECTASHIELD® mounting media (Vector Labs, Burlingame, Calif.). The stained slides were screened with a Nikon Eclipse E600 epifluorescent microscope and digital images collected with a SPOT digital camera (Diagnostic Instruments, Inc., Sterling Hgts, Mich.).

RT-PCR

RNA for use in RT-PCR analysis was isolated from infected liver as previously described (Lau et al., J. Parasitol. 87:19-23 (2001)). First-strand cDNA was generated from total RNA using the SuperScript First-Strand Synthesis System for RT-PCR kit (Life Technologies, Gaithersburg, Md.). The synthesis of cDNA was performed by priming RNA, isolated from the different parasite samples with either random hexamers or oligo-dt, and then incubation with reverse transcriptase (RT+). As a control for the presence of genomic DNA, reactions were done omitting the reverse transcriptase (RT−). Amplification of specific gene sequences was accomplished by PCR using a hot start Taq DNA polymerase from the HotStarTaq PCR kit (Quiagen, Valencia, Calif.). One microliter from the cDNA reaction was added to a PCR master mix with one of several oligonucleotide primer pairs including the following:

```
                                      (SEQ ID NO:02)
PfCS forward:    5' GATGATGGAAATAACGAAG 3';
                                      (SEQ ID NO:03)
PfCS reverse:    5' AGCACTGTTGGCATTAGC 3';

(SEQ ID NO:04)
PfLSA-1 forward: AATCTAACTTGAGAAGTGG;
                                      (SEQ ID NO:05)
PfLSA-1 reverse: CTGCATCGTCATTTATTATG;

(SEQ ID NO:06)
PfMSP-1 forward: 5' GACGAAGAAGATGATTCCTTAGTTG 3';
                                      (SEQ ID NO:07)
PfMSP-1 reverse: 5' TTTTGCTGGTGACGGAGGTG 3';.
```

The primers were designed and the specific conditions used for the PCR reactions were determined by using MacVector sequence analysis software (Accelrys, San Diego, Calif.). PCR products were electrophoresed on a 1% agarose gel, stained with ethidium bromide and the DNA bands visualized with an ALPHAIMAGER™ (Alpha Innotech Corporation, San Leandro, Calif.).

Laser Capture Microdissection

Liver stage parasites were isolated as described in Sacci et al. (2002) Mol. Biochem. Parasitol. 119, 285-28914. Briefly, frozen sections were cut from chimeric livers 5 days after P. falciparum infection and collected onto glass slides that had been treated with RnaseZap (Ambion, Austin, Tex.). The tissue sections were stained using the HISTOGENE™ LCM frozen section staining kit (Arcturus, Mountain View, Calif.) following the manufacture's recommended protocol. RNAse inhibitor (SUPERASE IN™, Ambion, Austin, Tex.) was included in all aqueous staining and washing steps to limit the possibility of RNA degradation. Individual schizonts were captured onto the thermoplastic membrane of CAPSURE™ HS LCM caps by melting of the membrane via laser activation. Typically, the laser spot size was 7.5 μm, the power 40 mW and the pulse duration 3 ms.

Total RNA, from cohorts of caps containing 100 laser microdissected schizonts, was isolated using the PICOPURE™ RNA isolation kit. (Arcturus, Mountain View, Calif.) following the manufactures' directions. Isolated RNA was then used for RT-PCR as described above.

Red Blood Cell Culture

Blood stage cultures were accomplished as described in Trager et al. (1976) Science 193, 673-675 with a few small modifications. Liver tissue from chimeric mice, infected 7 days previously with P. falciparum sporozoites, was aseptically collected and homogenized in 1 ml of RPMI 1640 culture medium. A portion of the homogenized tissue (100 μl) was added to red cell cultures, containing a 3% hematocrit, in 6-well tissue culture plates. The media was changed at 24 hours and blood smears were done at 24 and 48 hours after introduction of the liver homogenate, to identify blood stage parasites.

In Vivo Blood Stage Infections

Chimeric mice were injected with 1 ml i.p. of washed O$^+$ human red blood cells (huRBC) at a 50% hematocrit on day 6, 7 and 8 after infection with P. falciparum sporozoites. Blood smears were performed beginning on day 7 and were done daily until day 11 post infection. Blood smears were Giemsa stained or used in an immunofluorescent assay with parasite specific antisera as described above.

Example 1

A Small Animal (Mouse) Model of Plasmodium Malaria Liver Stage Infection

Plasmodium malaria is the predominant causative agent of the parasitic human disease malaria that infects an estimated 300 million people yearly and is responsible for millions of deaths per year. Development of newer and more effective anti malarial agents, preventive therapies and vaccines has been hampered by the limited animal models available for study of this form of malaria, especially of the obligate hepatic stage of malaria development. While mouse forms of malaria exist, P. falciparum malaria schizonts (liver stage infection) develop only in hepatocytes of human or some non-human primates. The invention provides a mouse model that yields a liver composed of a substantial proportion of human hepatocytes and is capable of supporting infection, growth and development of plasmodium parasites through the obligate liver stage.

SCID mice were crossed to mice with a urokinase type plasminogen activator (uPA) gene linked to an albumin promoter and bred to yield mice homozygous for both the SCID trait and the Alb/uPA transgene. Mice were transplanted with human hepatocytes via intrasplenic injection between days 4 and 15 of life. Animals were tested for human alpha-1 antitrypsin enzyme in serum at 4-8 weeks of life to confirm successful engraftment and expansion of human liver cells.

Mice of 8-12 weeks of age were inoculated with P. falciparum sporozoites from Anopheline mosquito salivary glands. Salivary glands of infected mosquitoes were microdissected, then homogenized and the sporozoites (1-3×10$^6$/mouse) injected intravenously into homozygous SCID/uPA mice that had been confirmed to have levels of human apha-1 antitrypsin in serum from 100-900 ug/L. Mice were sacrificed at 3-7 days post inoculation and liver and blood recovered for evaluation by immunofluorescence assay and RT-PCR.

Figure 2:
Figure 3:
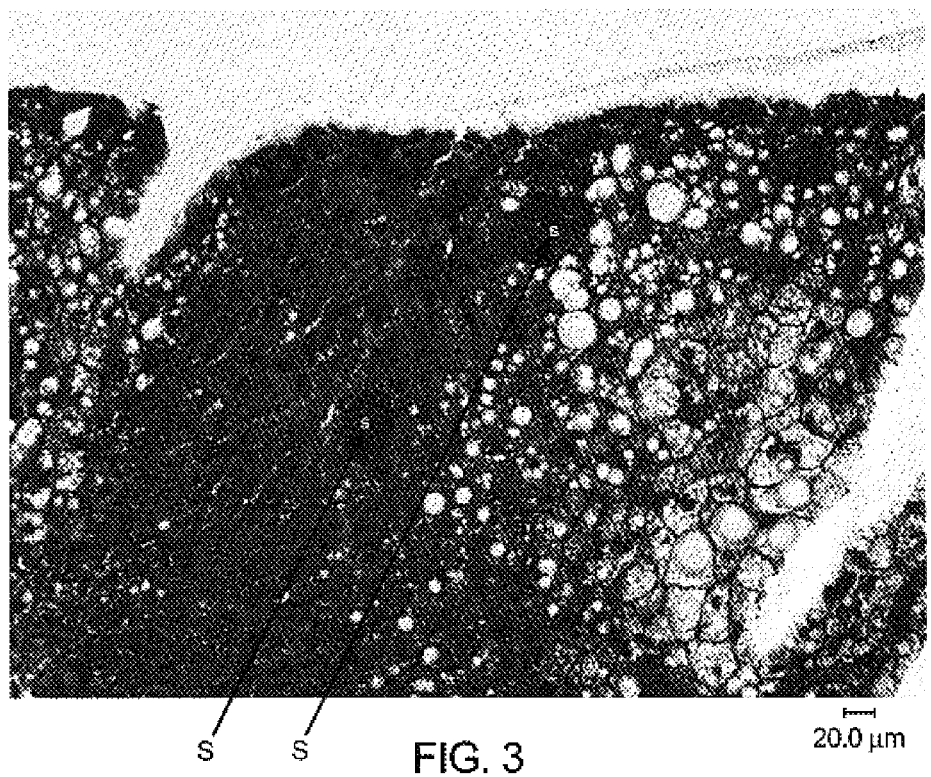
FIG. 3 is an exemplary section stained with an H & E type stain. Schizonts are labeled with an "S" and clearly demonstrate development of individual merozoites within the schizont.

FIGS. 1-3 provide exemplary results of liver tissue, sectioned and stained 6 days after infection. FIGS. 1 and 2 are images are from immunofluorescence assays using a parasite specific heat shock 70 monoclonal antibody, which only reacts with the hsp70 from blue counterstain. These images are classic for maturing liver stage schizonts. FIG. 3 is an exemplary section stained with an H & E type stain. Schizonts are labeled with an "S". The staining reveals developing merozoites in the schizont which is indicative of maturing parasites.

Example 2

Confirmation of *Plasmodium Falciparum* Malaria Hepatic Stage

Infection—Schizonts in Human Liver Cells in Chimeric Mice

Multiple confirmatory readouts were obtained to confirm *Plasmodium falciparum* liver stage infection.

Immunohistochemistry

Immunohistochemistry with antibodies specific for malarial antigens confirmed the presence of malarial schizonts from liver tissues recovered from mice on days 4, 5, 6 and 7 post inoculation. Malarial antigens confirmed in liver sections from 3 mice sacrificed at 6 days (hAAT 900), 6 days (hAAT 300), 5 days (hAAT 300) include:

1) a malarial heat shock protein (HSP) specific for liver stage infection with *plasmodium* malaria
2) LSA-1: a liver stage specific antigen (identified from a parasite DNA expression library by screening with sera from patients repeatedly bitten by infected mosquitoes while the patients were taking chloroquine prophylaxis)
3) EXP-1: a liver and blood stage antigen
4) AMA-1: an antigen present in sporozoites as well as liver and blood stage infection
5) circumsporozoite protein (CS protein).

CS protein was detected in the chimeric mice at 4 and 5 days post infection, but not on days 6 and 7. This is significant, since CS protein, which is prominent in the sporozoite, is lost in later stage (d 6) infection in the chimpanzee and mouse models (day 2 in mice), but not lost in prolonged in vitro infection.

Immunohistological study with antibodies recognizing 7 different malarial antigens (circumsporozoite protein-CS, heat shock protein 70-HSP70, exported protein 1:EXP-1, liver stage antigen 1:LSA-1, apical membrane 1:AMA-1, erythrocyte binding antigen 175:EBA-175) were performed as described in more detail below. These studies confirmed presence of malarial antigens in the liver of the chimeric mice on days 4, 5, 6 and 7 post inoculation. AMA-1 and EBA-175 are expressed in late stage liver schizonts. They were both negative on day 4, but appeared on day 5, with persistence on days 6, and 7 thus supporting progressive normal development of the malarial parasites during the liver stage infection in the mouse model.

Mice inoculated with *P. falciparum* sporozoites, intravenously, were euthanized at different timepoints (3, 4, 5, 6, 7 and 8 days), a portion of their liver was harvested and frozen in $LN_2$ for RNA isolation and the remaining tissue frozen in OCT for cryosectioning. In addition, the mice euthanized on day 7 and 8 received $5 \times 10^8$ human red blood cells, i-p, on day 6 and the day 8 mice received an additional $5 \times 10^8$ red blood cells on day 7 post parasite inoculation. These mice had blood collected at euthanasia for smears and isolation of RNA. This was an attempt to determine if merozoites were released from the mature liver stage schizonts and could invade red blood cells.

Demonstration of parasite infection was achieved by immunofluorescence assay (IFA) on methanol fixed cryosections with parasite specific antisera. The antigen recognized by the antibodies, source and expression during parasite development are presented in Table 1.

TABLE 1

| Antigen[1] | Source | Stage of Expression | | |
|---|---|---|---|---|
| | | Sporozoite | Liver | Blood Stage |
| CS protein | mAb | + | +[2] | − |
| SSP2 | mAb | + | +[2] | − |
| HSP70 | mAb | +/− | + | + |
| EXP-1 | polyclonal | − | + | + |
| LSA-1 | polyclonal | − | + | − |
| AMA-1 | polyclonal | − | +[3] | + |
| EBA-175 | polyclonal | − | +[3] | + |

[1]Circumsporozoite protein (CS protein), Sporozoite surface protein 2 (SSP2), Heat shock protein 70 (HSP70), Exported protein 1 (EXP-1), Liver stage antigen 1 (LSA-!), Apical membrane antigen 1(AMA-1), Erythrocyte binding antigen 175 (EBA-175).
[2]Expressed during early liver stage development.
[3]Expressed in late stage liver schizonts The stage specific expression, identified in Table 1 above, is based upon reports in the literature as well as experimental data from in vitro and in vivo infections done in Dr. Sacci's laboratory. Using this information as a guide, multiple IFAs were done with different anti-sera and the tissue sections from all the different time points.

Table 2 is a summary of the results, including the days post-infection on which tissue was collected, the dates the tissues were collected, and whether infection was confirmed.

TABLE 2

Assay Summary

| Number of Mice | Days Post-Infection | Tissues Collected | Infection Confirmed |
|---|---|---|---|
| 1 | 3 | Liver and Blood | Unconfirmed by IFA |
| 1 | 6 | Liver and Blood | IFA Positive |
| 1 | 4 | Liver and Blood | IFA Positive |
| 1 | 5 | Liver and Blood | IFA Positive |
| 1 | 7 | Liver and Blood | IFA Positive |
| 1 | 8 | Liver and Blood | Unconfirmed by IFA |

The results of the IFA assays are provided in Table 3. Using IFA, the presence of parasites demonstrated in chimeric livers 4, 5, 6 and 7 days after infection with multiple antisera. The expression patterns that were seen in mid to late stage parasites, by immunofluorescence, were consistent with expression patterns previously identified in *P. falciparum* infected chimpanzee liver (Guerin-Marchand et al., Nature 329:164-167 (1987); Szarfman et al., J. Exp. Med. 167:231-236 (1988)).

TABLE 3

Immunofluorescence Assay Results

| Antisera | Days Post-Infection | | | | | |
|---|---|---|---|---|---|---|
| | 3 | 4 | 5 | 6 | 7 | 8 |
| CS | neg | pos | pos | neg | neg | neg |
| SSP2 | neg | pos | pos/neg[+] | neg | neg | neg |
| HSP70 | neg | pos | pos | pos | pos | neg |
| EXP-1 | neg | pos | pos | pos | pos | neg |
| LSA-1 | neg | pos | pos | pos | pos | neg |
| AMA-1 | neg | neg | pos | pos | pos | neg |
| EBA-175 | neg | neg | pos/neg[++] | pos | pos | neg | pos = positive;
neg = negative
[+]Some schizonts displayed low levels of antibody staining, while other schizonts, in the same tissue section were negative for SSP2.
[++]Most schizonts displayed weak antibody staining, with some schizonts having no reactivity to the anti-EBA-175 antisera.

Figure 4:
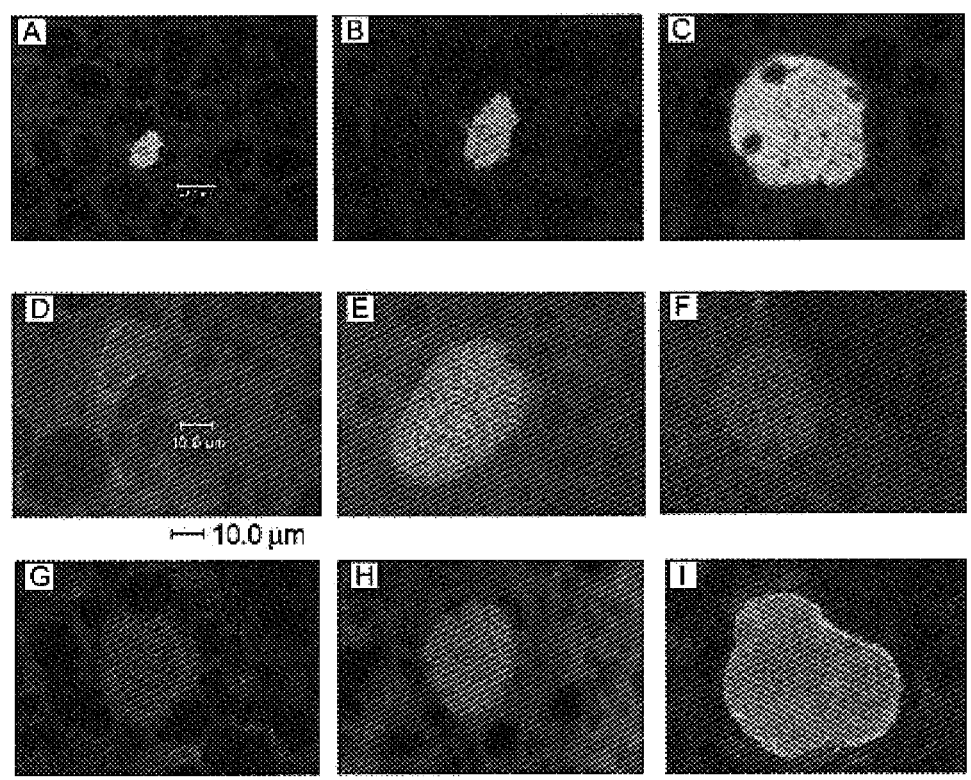
FIG. 4 is a series of immunofluorescent micrographs of chimeric SCID/AlbuPA liver cryosections post *P. falciparum* infection, stained with parasite specific antibodies. Tissue was harvested at 5 days (panels A, D, G), 6 days (panels B, E, H) and 7 days (panels C, F, I) after mice were inoculated with *P. falciparum* sporozoites. Sections in panels A, B and C were stained with an anti-PfHSP70 monoclonal antibody. Sections in panels D, E and F were stained with polyclonal rabbit antisera against the repeat region of LSA-1. Panel G, H, and I were stained with a polyclonal rabbit antisera against PfEBA-175. Magnification, ×400.

Representative fluorescent micrographs of the IFA results are presented in FIG. 4. Panels A, B and C are immunofluorescent assays, using an anti-*P. falciparum* heat shock protein 70 (PfHSP70) mAb, at 5, 6 and 7 days post infection. Panels D, E and F are micrographs of infected chimeric liver from days 5, 6, and 7 stained with Liver stage antigen-1 (LSA-1) anti-sera and Panels G, H and I are from days 5, 6 and 7 stained with an anti-*P. falciparum* erythrocyte binding antigen 1 (PfEBA-175) anti-sera. Both PfHSP70 and LSA-1 have been previously identified as being expressed in vivo (Guerin-Marchand et al., Nature 329:164-167 (1987); Szarfman et al., J. Exp. Med. 167:231-236 (1988)) and throughout in vitro development of the liver stage. PfEBA-175, initially identified as a ligand found on blood stage merozoites (Camus et al., Science 230:553-556 (1985)), was subsequently identified in the liver stage (Gruner et al., J. Infect. Dis. 184:892-897 (2001)) and appears during mid to late stage development. The differential reactivity of the parasites, demonstrated by IFA, clearly shows a change in the antigens that were expressed during the development of *P. falciparum* that took place in the hepatocytes.

PCR-Based Detection

To augment the IFA staining, a more sensitive RT-PCR analysis was done to identify the presence of parasite specific mRNA at the different time points. This also offered the opportunity to identify parasite-infected liver that was not seen by IFA at the 3 and 8-day time points. RT-PCR analysis was done using gene specific primers for the circumsporozoite protein (CS), Liver stage antigen-1 (LSA-1), and merozoite surface protein-1 (MSP-1) for chimeric mice infected for 4, 5, 6, 7 and 8 days. Primer sequences and conditions for the PCR reactions are described above in the methods section. RNA was extracted from tissue that had been flash frozen and stored at −80° C. Extracted RNA was treated with DNAse to remove any contaminating DNA that could produce a false positive. First strand cDNA reactions were done with and without oligo-dt priming to again control for the presence of contaminating DNA.

Figure 5:
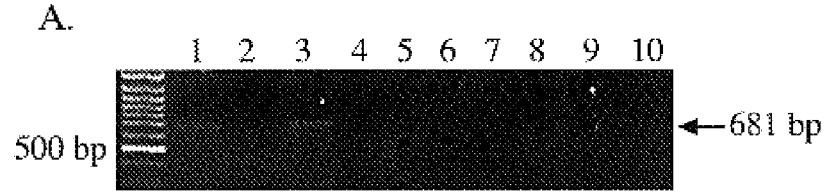
FIG. 5 is an RT-PCR analysis of *P. falciparum* infected chimeric human livers. RT-PCR was undertaken using primer sets for the circumsporozoite (CS) gene (panel A), LSA-1 (panel B) and MSP-1 (panel C). Tissue was collected at 4 days (lanes 1, 2), 5 days (lanes 3, 4), 6 days (lanes 5, 6) 7 days (lanes 7, 8) and 8 days (lanes 9, 10) after *P. falciparum* infection. Even numbered lanes are from RT-PCR assays in which the first strand reaction to generate cDNA included the reverse transcriptase. The odd numbered lanes were control assays in which the reverse transcriptase was left out of the first strand reaction. Lane 11 in panel B is a positive control LSA-1 PCR product from genomic DNA.
Figure 5:
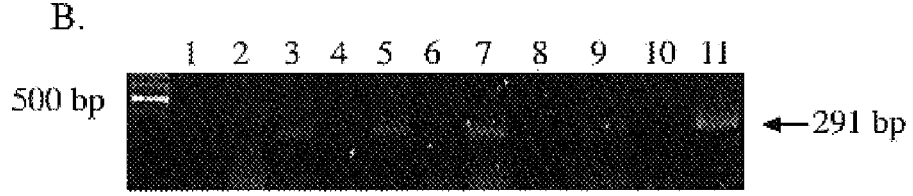
Figure 5:
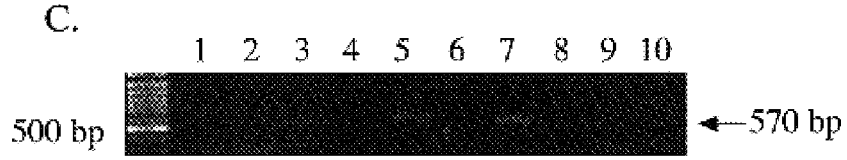

The results are provided in FIG. 5. RT-PCR using primer sets for the circumsporozoite (CS) gene are shown in Panel A, LSA-1 are shown in Panel B, and MSP-1 are shown in Panel C. Tissue was collected at 4 days (lanes 1, 2), 5 days (lanes 3, 4), 6 days (lanes 5, 6) 7 days (lanes 7, 8) and 8 days (lanes 9, 10) after *P. falciparum* infection. As shown in FIG. 5, RT-PCR analysis demonstrated the presence of CS message at days 4 and 5 post-infection, but not at later time points. This expression of message was consistent with the expression of CS antigen as demonstrated by IFA (Table 3) at 4 and 5 days after infection, and with a loss of expression at the later time points. This was distinct from in vitro *P. falciparum* infected human hepatocytes, in which CS expression was seen throughout the length of the culture and is typically used to identify infected hepatocytes in inhibition of liver stage development assays (ILSDA)(Charoenvit et al., Infect. Immun. 65:3430-3437 (1997)).

Genomic and Proteomic Confirmation of Liver Stage Infection

Laser capture microdissection is used to recover schizonts for

1. RT-PCR
2. western blotting
3. microarray

Confirmation of high quality PCR recovery will facilitate RT-PCR and microarray study to confirm the presence of orthologues of *falciparum* in the infected chimeric mouse livers as further support for liver stage infection.

Approximately 1000 captures of schizonts are anticipated to be necessary to provide sufficient protein for microarray analysis. Sections from the animals at 5 days post-infection have yielded up to 10 parasites/section as such approximately 100 sections may be needed.

The above work is repeated to provide for a consistent and reproducible model, and to further quantify the number of parasites in the liver stage of infection and the degree of variability in the model. Mice with variable levels of hAAT and diminishing numbers of malarial parasites to quantify the hAAT value correlated with malaria infection. The number of malaria parasites will be varied in order to determine the threshold of infection, i.e., the number of parasites needed to establish infection in the chimeric mouse livers. Animals are rechallenged approximately 2 weeks after infection to establish that repeated infection can occur in the mice as in human disease.

Example 3

Detection of Change in Life Stage of Malarial Parasites in the Mouse Model

The malaria-infected animal model was examined to detect the various stages of the malarial parasite, thereby showing that the malarial parasites exhibit the natural life cycle in the mouse model.

Development of Schizonts from Sporozoites in the Liver of Chimeric Mice

Immunohistochemistry and PCR for antigens and mRNA specific for life stages characteristic of delivery of infection by mosquito bite (sporozoite) and subsequent liver stage infection (schizonts) have confirmed that life stage development and change occurs in the chimeric mouse model of *plasmodium* malaria infection.

Immunofluorescence assays were carried out following standard protocols. Briefly, Liver tissue, frozen in OCT, was cut into 5 μm sections and placed onto glass slides. The tissue sections were fixed in ice-cold absolute methanol for 5 min. and air-dried. Sections were blocked with 3% normal goat serum and incubated with the appropriate primary antibody, at 37° C. for 30 min, in a humidified atmosphere. The slides were then washed 3 times in PBS and incubated with the appropriate fluorescein conjugated antibody diluted in 0.01% Evans blue, again for 30 min at 37° C. The slides were washed in PBS, mounted with a non-quench mounting media (VECTASHIELD®) and view with an epifluorescence microscope.

As shown in Table 4 below, multiple anti-sera were used to stain tissue sections form day 3-day 8 post-infection. It was apparent that the mouse infected for 3 days either did not develop an infection or the parasites were too small to be visualized (more likely there was no infection). The day 4-day 8 infections all showed varying reactivity's with the infected tissue. The results are consistent with the demonstrated expression of these antigens. CS and SSP2 are sporozoite antigens that are expressed during the early stages of development in the hepatocyte, but disappear subsequently. HSP70 is weakly expressed in sporozoites and strongly expressed in liver and blood stage parasites. LSA-1 is only expressed during the liver stage. EXP-1 is expressed throughout liver stage development and into the blood stage. AMA-1 and EBA-175 are primarily expressed in the blood stage, but are also found during the later stages of development in the hepatocyte. There is some recent evidence that AMA-1 is expressed in sporozoites, is down-regulated during early liver-stage development and then is up-regulated during the late stages of hepatic development.

TABLE 4

Immunofluorescence Assay Results

| Antisera | Days Post-Infection | | | | | |
|---|---|---|---|---|---|---|
| | 3 | 4 | 5 | 6 | 7 | 8 |
| CS | neg | pos | pos | neg | neg | neg |
| SSP2 | ND | pos | ND | ND | ND | ND |
| HSP70 | neg | pos | pos | pos | pos | neg |
| EXP-1 | neg | pos | pos | pos | pos | neg |
| LSA-1 | ND | ND | pos | pos | pos | neg |
| AMA-1 | neg | neg | pos | pos | pos | neg |
| EBA-175 | neg | neg | pos | pos | pos | neg |

Quantitation of liver stage infection is performed to further show that expansion of parasites occurs with infection of the mouse and development of liver stage (and subsequent blood stage) infection.

Passage of Liver Stage Infection to Blood Stage Infection

To evaluate the level of maturity that the chimeric liver schizonts achieved, an in vitro blood stage infection was initiated. Transmission of liver stage infection to blood stage infection, and thus the next stage of the *plasmodium* malaria life cycle, was detected in the malaria-infected animal model. The development of blood stage infection in *plasmodium* malaria has an obligatory intermediate liver stage: *P. malaria* must go through the schizont stage to develop to the blood stage infection. Detection of blood stage infection in the model shows evidence of the intermediate liver stage of infection as well as the liver and blood stages in the same model. The results further support use of the model while establishing a non-terminal readout that greatly facilitates efficacy experiments for antimalarial agents.

Figure 6:
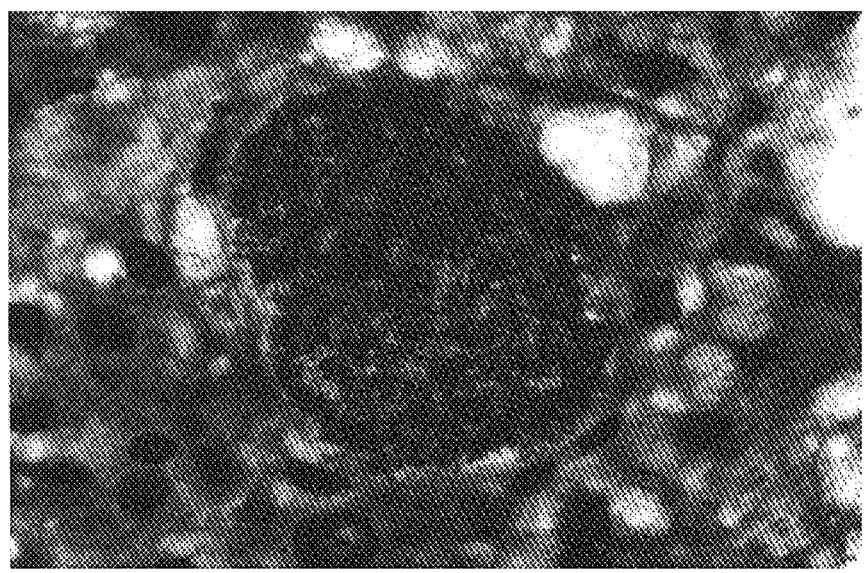
FIG. 6 is an exemplary chimeric liver tissue section from a SCID/Alb-uPA mouse 7 days after *Plasmodium falciparum* infection. A 7 μm frozen section was methanol fixed and Giemsa stained. A large, mature schizont occupies most of the field and contains clearly defined segmented nuclei. Magnification, ×1000.
Figure 7:
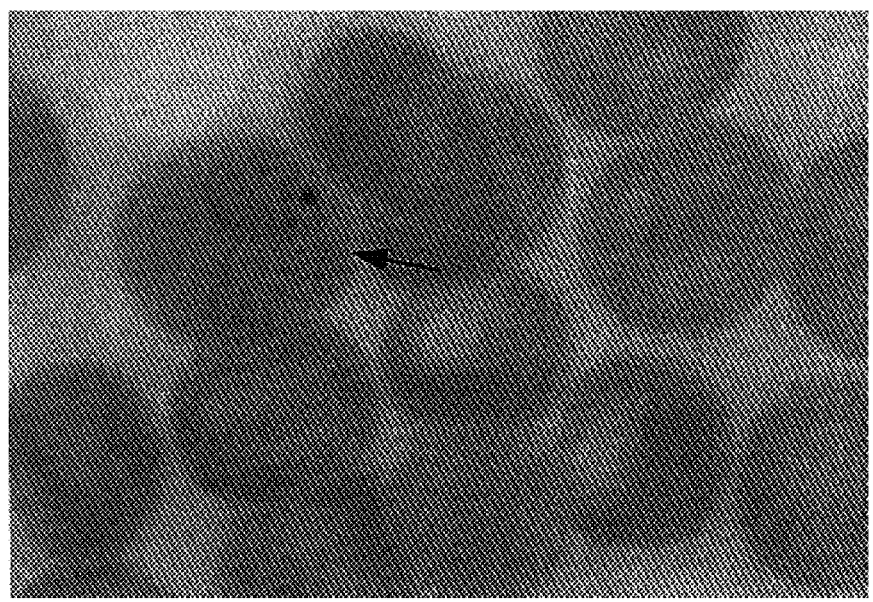
FIGS. 7-8 are Giemsa stained blood smears from an in vitro human red blood cell culture. Homogenized liver, from a SCID/Alb-uPA mouse, harvested 7 days after *P. falciparum* infection was added to a culture of human red blood cells. 24 hour later samples were taken and Giemsa stained. This micrograph shows a representative field from a stained smear with an infected red cell (arrow). The infected erythrocyte contains a developing trophozoite with a distinctive chromatin dot. Magnification, ×1000.
Figure 8:
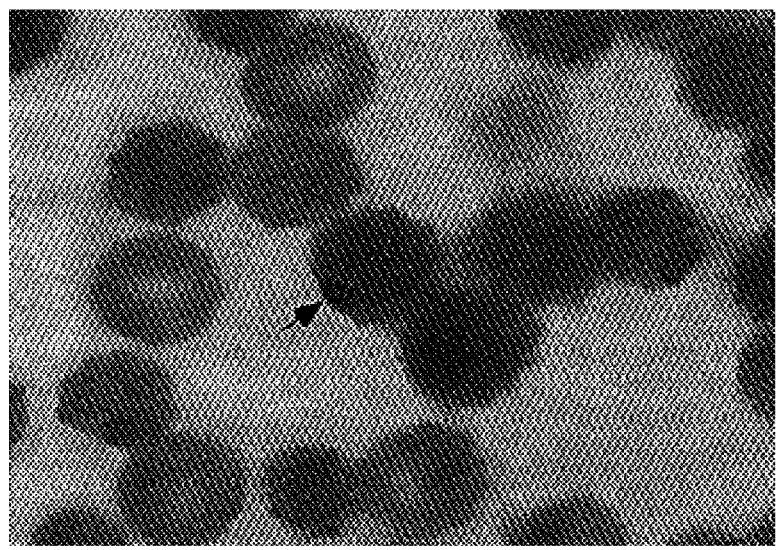

Mice were inoculated with $1\times10^6$ *Plasmodium falciparum* sporozoites. The animals were then euthanized on days 7 or 8 and had blood and liver collected for RT-PCR analysis and liver collected for cryosections. A portion of the livers from these days was also homogenized and added to human red cell cultures in vitro. The cultures were maintained as previously described (Trager et al., Science 193:673-675 (1976)) and smears were done starting at 24 hours after addition of the liver homogenate. Liver tissue collected 7 days after infection showed mature schizonts with clearly defined merozoites (FIG. 6), while tissue from 8 day infections lacked visible parasites, by microscopy. However, RT-PCR analysis of tissue from both days was positive for LSA-1 mRNA. Blood smears from cultures that received liver homogenates from 7 or 8-day infections showed the presence of ring stage parasites in the red blood cells at 24 hours after initiation of the cultures (FIG. 7 and FIG. 8). These results show that the liver stage merozoites were mature and capable of infecting red cells in vitro.

Figure 9:
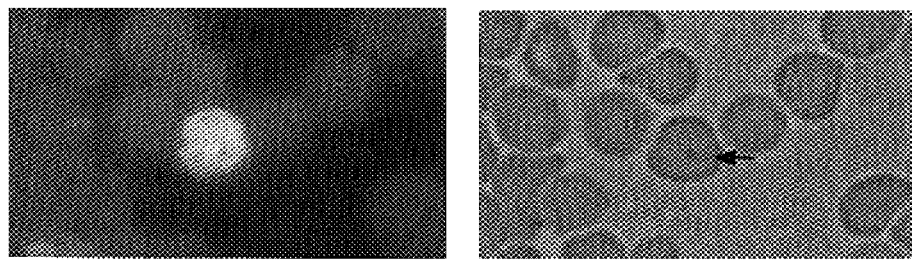
FIG. 9 is an immunofluorescent micrograph of a *P. falciparum* infected erythrocyte stained with an anti-exported protein 1 (EXP1) antibody. Human liver chimeric SCID/Alb-uPA mice were injected with human erythrocytes, I-P, starting at 6 days after inoculation with *P. falciparum* sporozoites. Panel A demonstrates very strong staining for (EXP1), while panel B is a phase contrast image of the same field. The arrow in panel B identifies the infected erythrocyte, which contains clear internal structure that is consistent with a developing parasite. Magnification, ×1000.

To show that the infection of red blood cells in vivo about $5\times10^9$ human red blood cells (RBCs) (1 ml of 50% hematocrit·O+human rbc) were injected intraperitoneally on 3-5 successive days to chimeric mice having liver stage malaria infection (e.g., days 6, 7, 8, and 10 post i.v.inoculation with *P. falciparum* sporozoites). Blood was subsequently colleted from infected mice for RNA isolation and smears of days 7, 8, 9, 10, and 11. Smears of peripheral blood or PCR of blood harvested at sacrifice were examined for malarial blood stage infection. The ability of the chimeric mouse model to support the complete *plasmodium* malaria life cycle was then assessed. Both thick and thin smears had blood stage parasites visible, with the day 11 smears showing a number of developing trophozoites and schizonts (FIG. 9) that could be visualized by Giemsa staining and IFA with an anti-*P. falciparum* exported protein 1 (PfEXP1) antibody.

The ability to establish human blood stage infection in vitro with liver stage parasites from the mouse model was examined by recovering chimeric mouse livers during liver stage infection, homogenizing the liver (e.g., by grinding it into pieces so as to break open liver cells and release parasites), and placing a portion of the liver sample into culture with human red blood cells. Giemsa stained slides of human red blood cells from cultures 24, 48, and 72 hours after introduction of homogenates from chimeric mouse livers 7 days after intravenous inoculation with *P. falciparum* from mosquito salivary glands confirmed presence of malarial parasites in human red blood cells.

Multiple infections, with different cohorts of mice and parasites, were used to assess the reproducibility of the mouse model after the first experimental group confirmed the parasite infection. In almost all cases (16/18), the mice demonstrated the presence of parasites in the chimeric livers from all time points (day 3-day 8 post infection) by IFA or RT-PCR. Interestingly, when compared to the HCV model the ability to establish an infection in the hepatocytes did not appear as dependent upon the level of hAAT in the mice as prior experience with HCV. While chimeric mice will only occasionally generate an HCV infection post inoculation if hAAT is <80 ug/ml and almost never if <60 ug/ml, with *P. falciparum* successful infections were demonstrated in mice that had levels from 25 µg/ml to 900 µg/ml. One infection study was done with mice that had received their hepatocyte transplants almost 6 months before they were infected with sporozoites. These results confirm the long-term stability of the transplant and its susceptibility to infection with the parasite.

To this point we have shown that the SCID/Alb-uPA chimeric mouse can reproducibly support liver stage infections and that the infected hepatocytes progress in the development of the parasite, as assessed by morphology, RTPCR, IFA and blood stage infection. The morphology (Meis et al., Exp. Parasitol. 70:1-11 (1990)) and gene expression appear to be very similar to that seen in *P. falciparum* infections of Chimpanzees at similar time points and the parasites become mature infective merozoites. Additionally, the late liver stage parasites seen in the chimeric mice were structurally and morphologically indistinguishable from those identified by Jeffery et al. (Am. J. Trop. Med. Hyg. 6:917-925 (1952) and Shortt et al.(Trans. Roy. Soc. Trop. Med. Hyg. 44:405-419 (1951)) in their studies to demonstrate the preerythrocytic stage of *P. falciparum* in human volunteers.

Example 4

LCM Isolation of *P. Falciparum* Liver Stage Parasites

Tissue sections containing liver stage parasites at day 5 post infection were used for laser capture microdissection (LCM), because the RT-PCR results identified this time point of the developing schizont as expressing message from genes that were associated with sporozoites, liver stages and blood stages of the parasites' lifecycle. Additionally, the parasites could be easily visualized by the standard staining protocol without more complex immunostaining.

Figure 10:
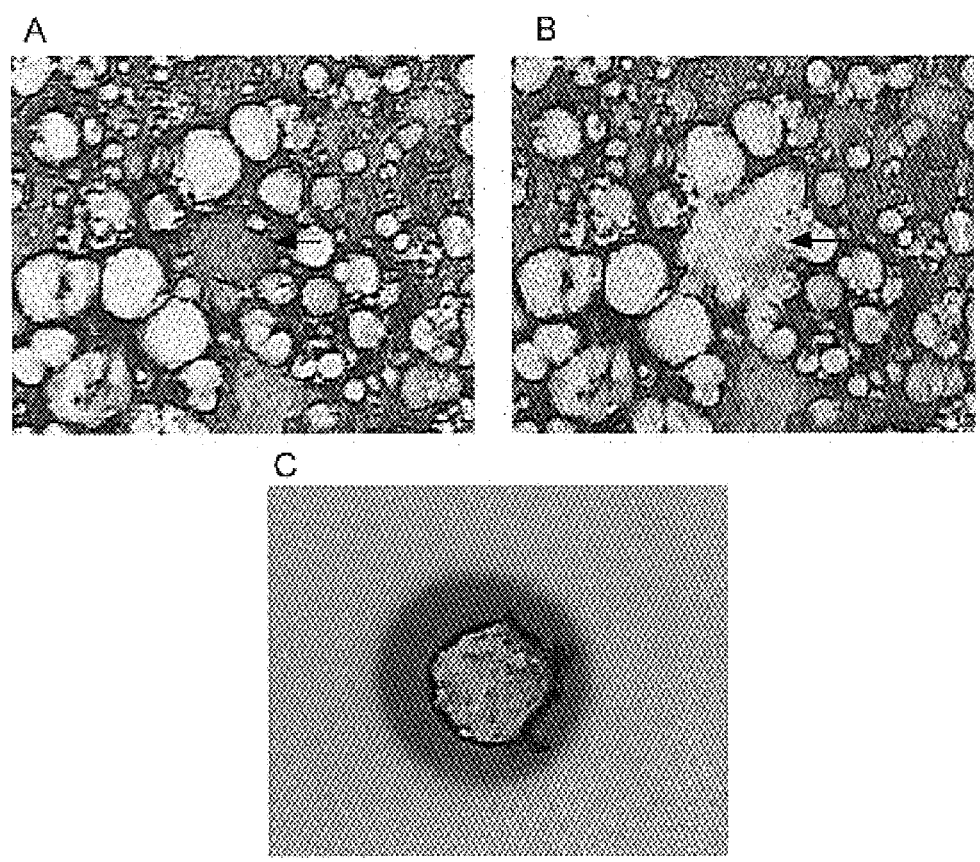
FIG. 10 shows laser capture microdissection images of *P. falciparum* infected SCID Alb-uPA mouse liver, 5 days post-inoculation. Panel A is a tissue section before laser pulse demonstrating the schizont (demarcated by the arrow), Panel B is the same area as in Panel A after membrane-schizont was removed, and Panel C shows the captured schizont.
Figure 11:
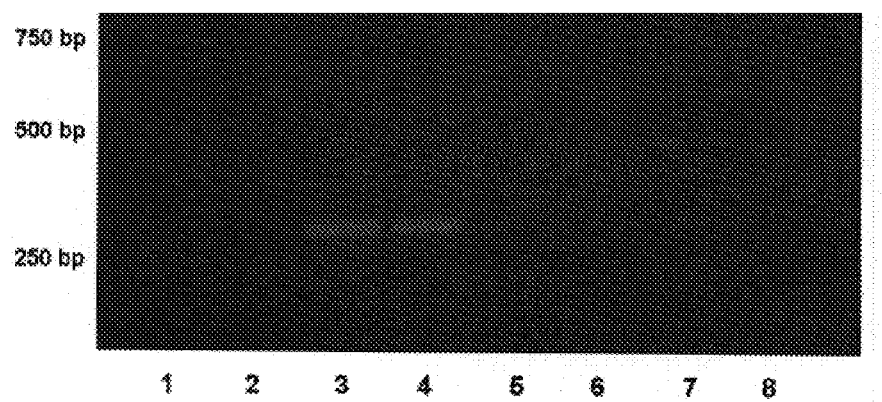
FIG. 11 RT-PCR analysis of RNA microdissected from *P. falciparum* infected Chimeric liver. Gene specific primers for LSA-1 and actin were utilized to amplify reverse transcribed RNA isolated from 5 day *P. falciparum* LCM schizonts (RT+) or DNA extracted from *P. falciparum* blood cultures (DNA). Control assays were also done in which the reverse transcriptase was left out of the first strand reaction (RT−) or water was used instead of a DNA template (−ve).

FIG. 10 demonstrates a representative isolation of an EE parasite. Panel A is the tissue section prior to laser activation, Panel B shows the same area after laser activation and the removal of the thermoplastic membrane containing the schizont, and Panel C is an image of the captured tissue. Total RNA was isolated and used to make cDNA for RT-PCR analysis from caps containing approximately 100 captures. Message for LSA-1 was easily amplified from the captured schizonts, while a band representing amplification of message for actin was barely visualized (FIG. 11). The results show that the recovered schizonts were virtually devoid of hepatocyte contamination and that intact parasite mRNA could be recovered for downstream analysis.

Example 5

Therapeutic Intervention in the Chimeric Mouse Model and Parallel to Clinical Outcomes Mice inoculated with malaria are treated with a known anti-malarial agent such as primaquine to establish effectiveness of this agent in the mouse model. Primaquine has a demonstrated effectiveness for the treatment of liver stage, and can be used as a positive control.

Example 6

Blocking of Invasion by Antibody

Confirmation that antibody can block invasion further establishes that passive immunotherapy can prevent infection during or after exposure in the animal model, and that the model can be used to facilitate vaccine development studies by establishing which antigens, when used as immunogens, yield antibodies or antibody profiles that can prevent infection with *plasmodium*.

Immune sera from volunteers are used to test for ability to block infection in the animal model. If variation in ability to block infection is seen (as is the case in in vitro studies), the antibody profiles from the different sera are examined to characterize effective sera. Such profiles provide patterns for passive immunotherapy for blockade with immune sera or immunoglobulin preparations.

Monoclonal antibodies to the parasite are assessed for the ability to block infection. Such antibodies have been very effective at blocking infection in vitro, but have not been examined in clinical settings. Effective blockade in the animal model indicates such approaches are viable clinical strategies and allow more directed work for vaccine development. Of particular interest is the ability of the monoclonal antibody 2A10 (available from the MR4 program at ATCC) to block infection.

Evidence that antibodies block malarial invasion in the in vivo model of *P. falciparum* infection of the invention provides assays for examining passive immunotherapy agents, and vaccine development for clinical application.

Example 7

Harvesting Malarial Parasites

The animal models can be used to generate high quality parasitic antigen preparations to further facilitate production of anti-malarial antibodies. Such antigens can be obtained from any stage of malarial infection of the animal, and can be obtained from the appropriate tissue according to methods well known in the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A chimeric, transgenic immunodeficient mouse infected with a human malarial parasite, the mouse comprising:
   a genomically integrated transgene, the transgene comprising a polynucleotide encoding a urokinase-type plasminogen activator polypeptide operably linked to a promoter such that the polypeptide is expressed in a mouse hepatocyte, wherein the mouse is homozygous for the transgene;
   a chimeric liver comprising human hepatocytes; and
   a malarial parasite infectious for a human in a cell of the liver;
   wherein the malarial parasites are present in the human hepatocytes of the chimeric liver.

2. The chimeric mouse of claim 1, wherein the mouse supports production of liver stage parasites following infection with a malarial sporozoite infectious for a human.

3. The chimeric mouse of claim 1, wherein the mouse supports development of schinozt stage parasites, including multiple merozoite stage parasites.

4. The chimeric mouse of claim 1, wherein the mouse supports development of erythrocytic stage malarial parasites.

5. The chimeric mouse of claim 1, wherein the infected mouse maintains detectable malarial parasites for a period of at least 6 days.

6. The chimeric mouse of claim 1, wherein the infected mouse maintains detectable malarial parasites for a period of at least 7 days.

7. The chimeric mouse of claim 1, wherein the promoter is an albumin promoter.

8. The chimeric mouse of claim 1, wherein the mouse is immunodeficient due to a scid mutation.

9. The chimeric mouse of claim 1, wherein the mouse has an at least partially intact innate immune system.

10. A method of producing a chimeric transgenic mouse infected with a human malarial parasite, the method comprising:
    implanting human hepatocytes into an immunodeficient, transgenic mouse, the mouse having a genome comprising a polynucleotide encoding a urokinase-type plasminogen activator polypeptide, wherein the polynucleotide is operably linked to a promoter, such that the polypeptide is expressed in mouse hepatocytes and wherein the mouse is homozygous for the polynucleotide; and
    inoculating the mouse with a human malarial parasite;
    wherein a chimeric transgenic mouse comprising a human-mouse chimeric liver and having human malarial parasites in human hepatocytes of the chimeric liver is produced.

11. A chimeric mouse host infected with a human malarial parasite produced by the method of claim 10.

12. A method for screening candidate agents for activity against a human malarial parasite, the method comprising the steps of:
    administering a candidate agent to the chimeric mouse of claim 1; and
    analyzing the effect of the candidate agent upon malarial infection;
    wherein a decrease in infectious load of the human malarial parasite relative to an untreated chimeric mouse host or relative to infectious load in the chimeric mouse prior to candidate agent administration is-indicative of anti-malarial activity of the agent.

13. The method of claim 12, wherein the candidate agent is administered prior to infection with a human malarial parasite.

14. A method of culturing a human malarial parasite, the method comprising:
    administering a human malarial parasite to the chimeric transgenic mouse of claim 1; and
    isolating human malarial parasites from the infected host following expansion of the human malarial parasite in the mouse.

15. A method of isolating human malarial parasite liver stage antigens, the method comprising:
    administering a human malarial parasite to the chimeric mouse of claim 1;
    isolating human malarial parasites from the infected host; and
    obtaining antigens from the malarial parasites.

* * * * *

UNITED STATES PATENT AND TRADEMARK OFFICE
CERTIFICATE OF CORRECTION

| | | |
|---|---|---|
| PATENT NO. | : 7,273,963 B2 | Page 1 of 1 |
| APPLICATION NO. | : 11/207176 | |
| DATED | : September 25, 2007 | |
| INVENTOR(S) | : Norman M. Kneteman | |

It is certified that error appears in the above-identified patent and that said Letters Patent is hereby corrected as shown below:

In Column 1 line 17: Delete "may have" and replace with --has--.

Signed and Sealed this

Eighth Day of July, 2008

JON W. DUDAS
*Director of the United States Patent and Trademark Office*

SEQUENCE LISTING

```
<160> NUMBER OF SEQ ID NOS: 7

<210> SEQ ID NO 1
<211> LENGTH: 15
<212> TYPE: PRT
<213> ORGANISM: Artificial Sequence
<220> FEATURE:
<223> OTHER INFORMATION: Multiple antigenic peptide (MAP)

<400> SEQUENCE: 1

Leu Glu Gln Glu Arg Leu Ala Lys Glu Lys Leu Gln Glu Gln Gln
1               5                   10                  15

<210> SEQ ID NO 2
<211> LENGTH: 19
<212> TYPE: DNA
<213> ORGANISM: Artificial Sequence
<220> FEATURE:
<223> OTHER INFORMATION: synthetic primer

<400> SEQUENCE: 2
gatgatggaa ataacgaag                                                    19
```

```
<210> SEQ ID NO 3
<211> LENGTH: 18
<212> TYPE: DNA
<213> ORGANISM: Artificial Sequence
<220> FEATURE:
<223> OTHER INFORMATION: synthetic primer

<400> SEQUENCE: 3
agcactgttg gcattagc                                              18

<210> SEQ ID NO 4
<211> LENGTH: 19
<212> TYPE: DNA
<213> ORGANISM: Artificial Sequence
<220> FEATURE:
<223> OTHER INFORMATION: synthetic primer

<400> SEQUENCE: 4
aatctaactt gagaagtgg                                             19

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
ctgcatcgtc atttattatg                                            20

<210> SEQ ID NO 6
<211> LENGTH: 25
<212> TYPE: DNA
<213> ORGANISM: Artificial Sequence
<220> FEATURE:
<223> OTHER INFORMATION: synthetic primer

<400> SEQUENCE: 6
gacgaagaag atgattcctt agttg                                      25

<210> SEQ ID NO 7
<211> LENGTH: 20
<212> TYPE: DNA
<213> ORGANISM: Artificial Sequence
<220> FEATURE:
<223> OTHER INFORMATION: synthetic primer

<400> SEQUENCE: 7
ttttgctggt gacggaggtg                                            20
```